United States Patent
Emond et al.

(10) Patent No.: US 11,415,493 B2
(45) Date of Patent: Aug. 16, 2022

(54) DETECTION OF CELLS IN A LIQUID SAMPLE

(71) Applicant: DELTA INSTRUMENTS B.V., Drachten (NL)

(72) Inventors: Pierre Laurent Emond, Amherst, NH (US); Nancy Gail Perlmutter, Wellesley, MA (US); James Willis Kreider, Newton, MA (US)

(73) Assignee: PERKINELMER HEALTH SCIENCES B.V., Groningen (NL)

( * ) Notice: Subject to any disclaimer, the term of this patent is extended or adjusted under 35 U.S.C. 154(b) by 640 days.

(21) Appl. No.: 16/085,194

(22) PCT Filed: Mar. 17, 2017

(86) PCT No.: PCT/IB2017/000364
§ 371 (c)(1),
(2) Date: Sep. 14, 2018

(87) PCT Pub. No.: WO2017/158431
PCT Pub. Date: Sep. 21, 2017

(65) Prior Publication Data
US 2019/0086301 A1 Mar. 21, 2019

(30) Foreign Application Priority Data
Mar. 17, 2016 (EP) .................... 16160837

(51) Int. Cl.
| | | |
|---|---|---|
| *G01N 1/30* | (2006.01) |
| *C12Q 1/04* | (2006.01) |
| *A01B 5/02* | (2006.01) |
| *C12M 1/34* | (2006.01) |
| *B01L 3/00* | (2006.01) |
| *C09B 11/28* | (2006.01) |
| *C09B 23/04* | (2006.01) |
| *C12Q 1/68* | (2018.01) |
| *G01N 21/64* | (2006.01) |

(52) U.S. Cl.
CPC ............... *G01N 1/30* (2013.01); *A01B 5/02* (2013.01); *B01L 3/5023* (2013.01); *B01L 3/50273* (2013.01); *C09B 11/28* (2013.01); *C09B 23/04* (2013.01); *C12M 1/34* (2013.01); *C12Q 1/04* (2013.01); *C12Q 1/68* (2013.01); *G01N 21/6486* (2013.01)

(58) Field of Classification Search
CPC .............. G01N 1/30; C12Q 1/04; C12Q 1/68
See application file for complete search history.

(56) References Cited

U.S. PATENT DOCUMENTS

| | | |
|---|---|---|
| 3,679,365 A | 7/1972 | Wrightman et al. |
| 4,587,213 A | 5/1986 | Malecki |
| 4,880,915 A | 11/1989 | Kajihara et al. |
| 5,288,642 A | 2/1994 | Turner |
| 5,572,946 A | 11/1996 | Holroyd |
| 5,773,299 A | 6/1998 | Kim et al. |
| 5,798,221 A * | 8/1998 | AEgidius ............... C12Q 1/04 252/301.16 |
| 6,157,692 A | 12/2000 | Christensen et al. |
| 6,165,742 A | 12/2000 | Øfjord et al. |
| 6,511,819 B2 | 1/2003 | Tryland et al. |
| 6,660,469 B1 | 12/2003 | Wright et al. |
| 7,550,567 B2 | 6/2009 | Metzner et al. |
| 7,601,498 B2 | 10/2009 | Mao et al. |
| 7,794,968 B2 | 9/2010 | Jelinek |
| 7,803,943 B2 | 9/2010 | Mao et al. |
| 8,026,079 B2 | 9/2011 | Yoshida et al. |
| 2004/0157211 A1 | 8/2004 | Skyggebjerg et al. |
| 2005/0032129 A1 | 2/2005 | Hasui |
| 2006/0211028 A1* | 9/2006 | Mao .................. C12Q 1/6851 435/6.11 |
| 2006/0211029 A1 | 9/2006 | Mao et al. |
| 2009/0011458 A1 | 1/2009 | Johnson |
| 2009/0131279 A1 | 5/2009 | Rueck et al. |
| 2009/0226880 A1* | 9/2009 | Anderson ............ C12N 5/0612 435/2 |
| 2009/0255473 A1 | 10/2009 | Katz et al. |
| 2010/0233710 A1 | 9/2010 | McDougall et al. |
| 2014/0342366 A1 | 11/2014 | Yehualaeshet et al. |
| 2015/0056625 A1 | 2/2015 | Pautz et al. |

(Continued)

FOREIGN PATENT DOCUMENTS

| | | |
|---|---|---|
| EP | 0 342 501 | 11/1989 |
| EP | 0 750 678 | 9/1999 |
| EP | 1 918 385 | 6/2011 |

(Continued)

OTHER PUBLICATIONS

Lebaron et al., Effectiveness of SYTOX Green Stain for Bacterial Viability Assessment. Applied and Environmental Microbiology 64(7) : 2697-2700 (Year: 1998).*
Wright et al., Establishing benchmarks in compliance assessment for the ballast water management convention by port state control. J of Marine Engineering & Technology 14(1) :9-18 (Year: 2015).*
Becker et al., In situ Screening Assay for Cell Viability using a Dimeric Cyanine Nucleic Acid Stain. Analytical Biochemistry 221(1) : 78-84 (Year: 1994).*

(Continued)

*Primary Examiner* — Ethan C Whisenant
(74) *Attorney, Agent, or Firm* — Nixon & Vanderhye P.C.

(57) ABSTRACT

The invention relates to a method for counting cells, such as bacteria and/or somatic cells in liquid samples, such as in dairy products, preferably raw milk. Disclosed is a method comprising a combination of steps that apply dimeric nucleic acid dyes that normally do not penetrate cells (=cell-impermeant dyes), which are rendered cell-permeant by using the right combination of pH, buffer and temperature.

20 Claims, 23 Drawing Sheets

(56) References Cited

U.S. PATENT DOCUMENTS

| | | | |
|---|---|---|---|
| 2015/0111216 A1 | 4/2015 | Delahunt et al. | |
| 2016/0376581 A1* | 12/2016 | Richmond | B01J 41/07 435/6.12 |

FOREIGN PATENT DOCUMENTS

| | | |
|---|---|---|
| EP | 1 863 933 | 10/2011 |
| EP | 2 565 281 | 7/2016 |
| JP | 3406608 | 3/2003 |
| WO | 95/25174 | 9/1995 |
| WO | 00/12750 | 3/2000 |
| WO | 02/08454 | 1/2002 |
| WO | 2009038607 | 3/2009 |
| WO | 2009/064943 | 5/2009 |

OTHER PUBLICATIONS

Kahraman et al., Nanoclay Dispersion into a Thermosetting Binder Using Sonication and Intensive Mixing Methods. J. of Applied Polymer Science 129 : 1773 (Year: 2013).*

Koh et al., A Comparison of the Effectiveness of Sonication, High Shear Mixing and Homogenisation on Improving the Heat Stability of Whey Protein Solutions. Food Bioprocess Technology 7 :556-566 (Year: 2014).*

Rawlings et al., Families of Serine Peptidases. Methods in Enzymology 244: 19 (Year: 1994).*

Sonmezoglu et al. Nucleosides, Nucleotides and Nucleic Acids 34:515 (Year: 2015).*

International Search Report for PCT/IB2017/000364, dated Jul. 18, 2017, 5 pages.

Written Opinion of the ISA for PCT/IB2017/000364, dated Jul. 18, 2017, 7 pages.

Haines et al., "Properties of nucleic acid staining dyes used in gel electrophoresis", Proteomics, vol. 36, No. 6, Mar. 23, 2015, pp. 941-944.

Marentis et al., "Microfluidic sonicator for real-time disruption of eukaryotic cells and bacterial spores for DNA analysis", Ultrasound in Medicine and Biology, vol. 31, No. 9, 2005, pp. 1265-1277.

Duffy et al., "Viability staining in a direct count rapid method for the determination of total viable counts on processed meats", Journal of Microbiological Methods, vol. 31, No. 3, 1998, pp. 167-174.

Sayas et al., "Toxicity, mutagenicity and transport in *Saccharomyces cerevisiae* of three popular DNA intercalating fluorescent dyes", Yeast, vol. 32, No. 9, 2015, pp. 595-606.

Chiaraviglio et al., "Evaluation of Impermeant, DNA-Binding Dye Fluorescence as a Real-Time Readout of Eukaryotic Cell Toxicity in a High Throughput Screening Format", Assay and Drug Development Technologies, vol. 12, No. 4, 2014, pp. 219-228.

Gunasekera et al., "a Flow Cytometry Method for Rapid Detection and Enumeration of Total Bacteris in Milk", Applied and Environmental Microbiology, Mar. 2000, pp. 1228-1232.

DiGiulio et al., "Prevalence and Diversity of Microbes in the Amniotic Fluid, the Fetal Inflammatory Response, and Pregnancy Outcome in Women with Preterm Prelabor Rupture of Membranes", American Journal Reprod Immunol., Jul. 1, 2010, 64(1): 38-57. 2010.

Goodridge et al., "The use of a fluourescent bacteriophage assay for detection of *Echerichia coli* O157:H7 in food", International Journal of food microbiology, 1999, vol. 47, pp. 43-50.

Paape et al., "Variation of estimated numbers of milk somatic cells stained with Wright's stain or pyroninY-methyl green stain", Journal of dairy science, 1963, 46(11), pp. 1211-1216.

Veal et al., Fluorescence staining and flow cytometry for monitoring microbial cells, Journal of immunological methods, 2000, 243, pp. 191-210.

Safety Report of GelRed and GelGreen, Nucleic Acid Detection Technologies, Bitium, pp. 1-11, Oct. 16, 2013.

* cited by examiner

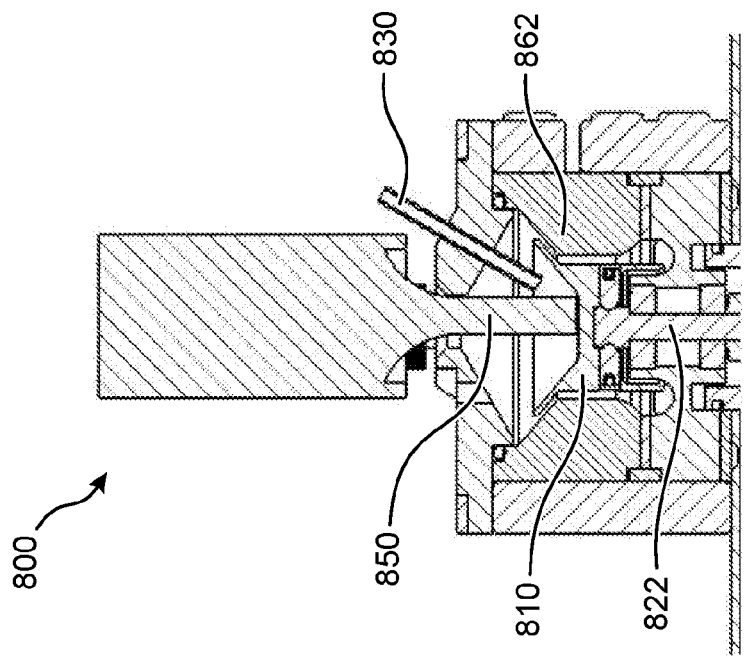
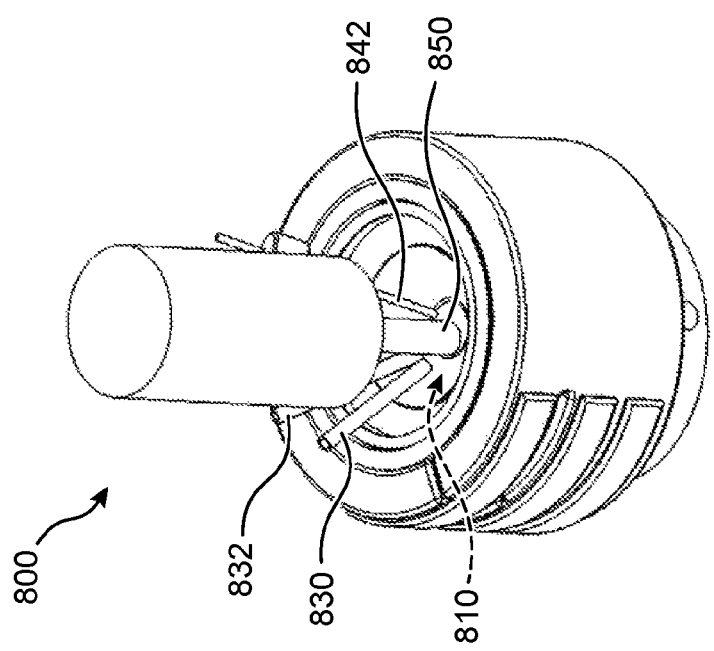
Fig. 8B
Fig. 8A

DETECTION OF CELLS IN A LIQUID SAMPLE

This application is the U.S. national phase of International Application No. PCT/M2017/000364 filed Mar. 17, 2017 which designated the U.S. and claims priority to European patent application Serial No. EP18160837.7 filed 17 Mar. 2016 the entire contents of each of which are hereby incorporated by reference.

RELATED APPLICATIONS AND INCORPORATION BY REFERENCE

This application claims benefit of European patent application Serial No. EP16160837.7 filed 17 Mar. 2016.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The invention relates to methods and means for the rapid quantitation of cells, such as, somatic cells and/or microorganisms in liquid samples, such as biological fluids. More in particular, the present invention relates to methods and means for counting bacteria in raw milk by applying a fluorescent dye.

BACKGROUND OF THE INVENTION

There is a continuous need for the ability to detect and quantify microorganisms (especially living bacterial cells) in the food, beverage, pharmaceutical, environmental, manufacturing and clinical industries. In agriculture, the presence of bacteria such as *Staphylococcus aureus*, may cause mastitis in cows and may be harmful for consumers when present in milk. Mastitis detection itself is frequently based on the counting of somatic cells (leukocytes: white blood cells and epithelial cells) that migrate into the milk during mastitis. It is generally acceptable to have between 0 and 500,000 somatic cells per cc in normal milk (not related to the presence of mastitis), whereas a number of over 1 million somatic cells per cc is certainly indicative of mastitis. The art teaches a variety of methods to determine the number of somatic cells in milk, which in turn is clearly an indication that the milk is unsuitable for human consumption.

Besides the fact that it is important to be able to determine the number of somatic cells to detect whether the milk is from a cow suffering from mastitis, it also goes without saying that it is vitally important to monitor the number of any type of bacteria in biological fluids such as (raw and/or processed) milk to ensure that it is safe for human consumption. The art teaches many different ways of detecting bacteria in liquid samples such as dairy products like milk.

The traditional approach to detect and enumerate bacteria in raw milk is through a standard plate count method, which takes approximately 48 hours. This procedure results in a number of colony forming units (CFUs) per unit volume. It is clearly desirable to use an equally reliable but much more rapid method for counting and enumerating microorganisms in milk than this standard plate count method.

EP0750678B1 discloses a method for detecting bacteria in liquid samples by using a composition comprising a mixture of an ion-chelating agent, a proteolytic enzyme, a detergent and a bacteriologically specific fluorochrome. This mixture causes lysis of the cells, degrades and solubilizes the protein particles and cell debris and stains the bacteria in the sample. Numbers are counted by using a subsequent flow cytometry step. The disadvantage of this method lies in the number of agents that are used (including an ion-chelating agent and a detergent). In the procedure fluorochromes are used that are known to penetrate cells, such as ethidium bromide, which is a toxic agent. The use of toxic agents results in cumbersome waste handling and higher costs per sample. It is generally desirable to use non-toxic reagents.

WO02/08454 discloses a method for determining the percentage of viable cells contained within a liquid sample by using a dye that is detectably altered by enzymatic activity of the viable cells (such as fluorescein diacetate or Oregon Green™), thereby comparing the number of viable to the number of non-viable cells. The disadvantage of this method is that it is time consuming as it requires centrifugation and a dye is used that depends on the viability of the cells and can therefore not detect all cells, including certain living cells.

WO00/12750 discloses a method for evaluating the presence of bacteria in milk by incubating the milk with a culture medium comprising a fluorogenic substrate that forms a detectable fluorogenic product upon interaction with the bacteria. This method has the disadvantage that the incubation period between bacteria and fluorogenic substrate takes at least 7 hours, which is too long for rapid processing of milk products.

Others have used systems in which Polymerase Chain Reaction (PCR)-based or Loop-mediated isothermal amplification (LAMP) technologies are applied to determine the presence of bacteria in liquid protein-containing samples such as milk. Many of these nucleic acid amplification/detection procedures take time and sometimes require the breakdown of the bacteria and extraction and/or precipitation of the genetic material, which makes these procedures generally complex and cumbersome.

WO2013/083754 discloses a method for the detection of bacteria in milk wherein (specific) antibodies are used that interact with the bacteria, and which can then be detected thereafter with a staining procedure. The disadvantage of using this method is the staining procedure and the use of specific antibodies against specific bacteria (that might miss bacteria not bound to such antibodies). In other words, one desires to count all bacteria that are present in milk, while antibodies always have some kind of specificity for one antigen, but not for another. Moreover, the relative high costs that come with using (recombinant) antibodies is an additional disadvantage of that procedure.

JP2013081424 discloses a method in which a sample needs to be de-proteinized by isoelectric precipitation and further requires filtration after which the (live) bacteria can be detected using a fluorescent reagent. The disadvantage in that particular method lies in the complicated de-proteinization and purification method that takes time.

EP1918385B1 discloses a method of detecting bacteria in a liquid sample by flow cytometry in which the sample is initially treated with a lipolytic enzyme and proteases, followed by a step of treating the sample with a topoisomerase poison and/or a DNA gyrase poison, after which the DNA is stained with a nuclear staining agent. This method has the disadvantage of using multiple and costly dyes, and time: the different steps add up to a procedure that will last between 1 and 48 hours.

Gunasekera et al. (A flow cytometry method for rapid detection and enumeration of total bacteria in milk, 2000. *Appl Environ Microbiol* 66(3):1228-1232) discloses the use of SYTO® BC as a fluorescent nucleic acid staining agent, treatment with a protease (Savinase®) to clear the protein globules in milk and subsequent flow cytometry to detect and enumerate bacteria in UHT and raw milk samples. The disadvantage of this method is that Gunasekera et al, discloses an additional centrifugation step, which takes time and is cumbersome in rapid detection systems. In fact, the method disclosed by Gunasekera et al. takes approximately 60 minutes before final analysis. This is still a relatively long procedure.

US 2015/0056625 A1 discloses reagents for clarification of emulsions (water/fat mixtures) to enable subsequent measurements of cells in such emulsions.

CN101050416 describes a microscopic examination method to detect bacteria in milk, with a smearing apparatus, a dying apparatus, a washing/drying apparatus, and a microscopic detecting apparatus using a glass slide.

None of the above methods known in the art teach a procedure that is fast, requires only a few steps, that is reliable, in-expensive and safe. Despite the methods and means available in the art and listed above, there remains a need for a high-throughput, safe, fast and reliable method to detect bacterial material in biological fluids such as (raw) milk. Many of the listed methods are either slow, use toxic reagents, are cumbersome and/or expensive, which makes them less suitable for large production processes and high-throughput screenings.

Citation or identification of any document in this application is not an admission that such document is available as prior art to the present invention.

SUMMARY OF THE INVENTION

The present invention relates to a method of counting cells in a liquid sample, said method comprising the steps of:
a) mixing a staining composition comprising a dimeric nucleic acid dye and a buffering agent with said sample;
b) optionally sonicating the mixture of step a);
c) incubating the mixture at a temperature from about 45° C. to about 95° C. for less than 10 minutes;
d) optionally sonicating the incubated mixture of step c); and
e) counting the cells that are stained with said dye within said mixture, or a part thereof,
wherein the nucleic acid has the formula Q1-BRIDGE-Q2, wherein Q1 and Q2 are nucleic acid dye moieties and BRIDGE is connecting Q1 and Q2. The advantage of this method is that it is fast, reliable and uses safe nucleic acid dyes which are cell-impermeant and non-mutagenic and therefore safe in use. The problem of making these dyes cross the cell membrane of whole cells in order to be able to count these cells is solved by the present invention.

In a preferred embodiment, the dimeric nucleic acid dye is capable of binding to DNA via a release-on-demand mechanism.

Further preferred embodiments relating to preferred compositions of the staining composition, preferred chemical nature of BRIDGE, Q1 and Q2, preferred conditions of the incubation step c) in respect of temperature and pH and the preferred way of counting the cells are defined in the claims.

In a preferred embodiment, said cells are somatic and/or bacterial cells. In another preferred embodiment, said liquid sample is a biological sample selected from the group consisting of milk, blood, urine, saliva, feces and spinal fluid. Especially animal milk samples, such as raw milk samples are preferred for determining the number of bacterial and/or somatic cells in that raw milk, to determine whether a cow suffers from mastitis and/or whether a milk sample is suitable for human consumption. In another aspect of the invention, said liquid sample is an environmental sample, such as waste water.

In yet another aspect, the invention relates to an apparatus as defined in claims.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 8A schematically shows a three dimensional view of a mixing unit of an apparatus for counting cells in a liquid sample. FIG. 8B schematically shows a cross-sectional view of the mixing unit of FIG. 8A.

DETAILED DESCRIPTION

Figure 1:
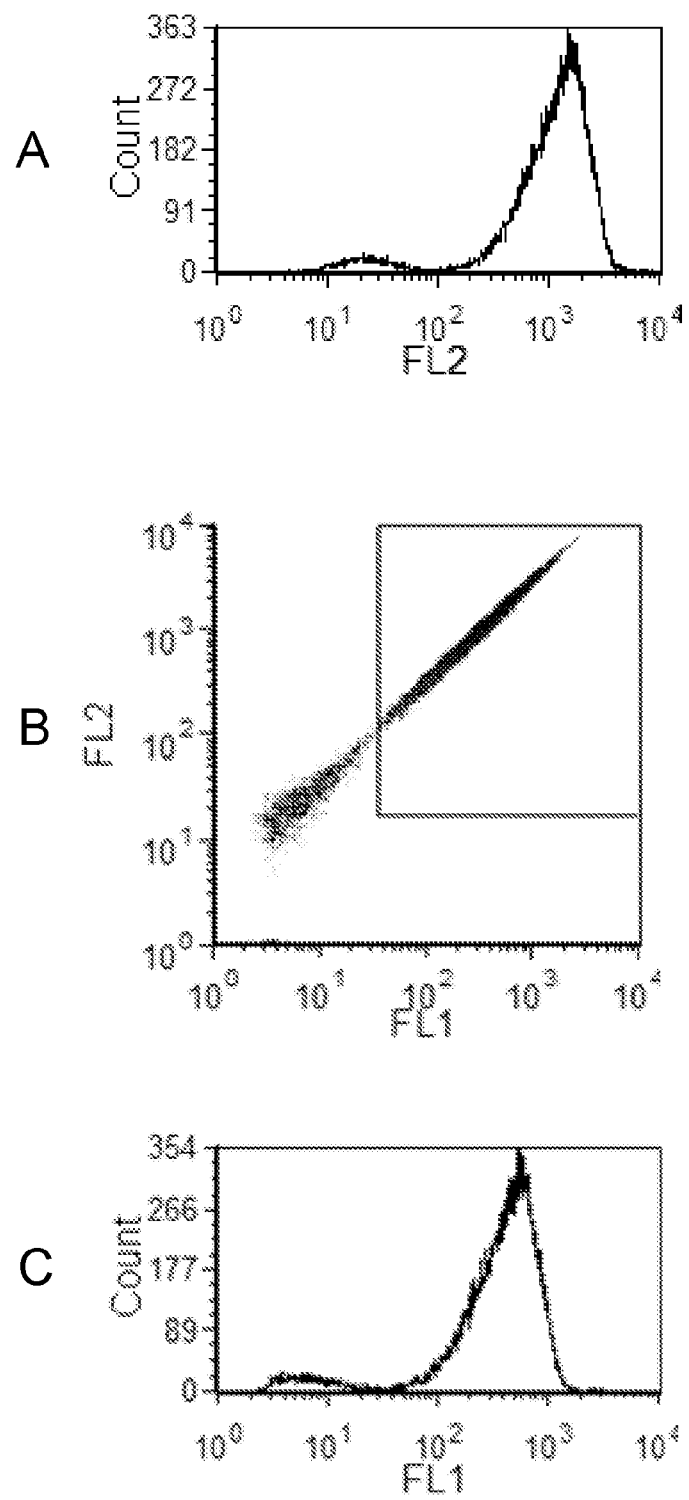
FIG. 1 shows flow cytometer data of stained *E. coli*. The three fluorescence detectors in the flow cytometer had the following optical filters; 527 nm Bandpass (FL1), 590 nm Bandpass (FL2), and a 630 nm Longpass (FL3). The FL1 and FL2 fluorescence channels were used to identify stained bacteria (C and A respectively). A rectangular region was defined around the positively stained cells identified as the stained *E. coli* cells in the FL1 versus FL2 two-dimensional correlation plot (B).

A diverse range of microorganisms are typically found in milk, including gram-positive, gram-negative, aerobic, anaerobic and micro-aerobic bacteria, which grow in varying cell arrangements and have sizes ranging from approximately 0.5 to 8 microns in diameter. The precise composition and number of bacteria in raw milk can vary geographically and seasonally. In view of this, and the disadvantages known to the (standard) methods used in the art as described above, a relatively simple, safe and rapid method is needed to detect the vast range of bacteria found in milk without interference from other materials that are normally present in raw milk. However, the complexity of a biological fluid, and especially raw milk makes the rapid detection, counting and enumeration of bacteria contained therein difficult, especially when using fluorescent dyes. Milk has the property of exhibiting an inherent background fluorescence due to the presence of certain components such as riboflavin and beta carotenes. When fluorescent dyes are used to stain bacteria in milk samples, such dyes can also non-specifically bind to milk fat globules that have associated outer protein membranes. This obviously may result in an increase in background fluorescence signal hampering a proper read-out.

Of specific relevance is the small genome size of bacteria which can range from approximately 2 to 8 Mega base pairs (Mbp), as compared to the approximately 3 Giga base pairs in mammalian cells.

The present invention relates to a fast and reliable and safe method for counting cells in a liquid sample using a dye that is safe in the sense that human cells are not permeable for this dye. The method of the invention renders the cells to be counted permeable for the dye only in the reaction container (also referred to as mixing cup) comprising the cells to be counted. The present invention is suitable for fast and reliable counting of cells, even in biological liquid samples, such as (raw) milk that may contain fat, cells, proteins and minerals. The method for counting cells in a liquid sample according to the present invention comprises the steps of:
a) mixing a staining composition comprising a dimeric nucleic acid dye and a buffering agent with said sample;
b) optionally sonicating the mixture of step a);
c) incubating the mixture at a temperature from about 45° C. to about 95° C. for less than 10 minutes;
d) optionally sonicating the incubated mixture of step c); and
e) counting the cells that are stained with said dye within said mixture, or a part thereof,
wherein the nucleic acid has the formula Q1-BRIDGE-Q2, wherein Q1 and Q2 are nucleic acid dye moieties and BRIDGE is connecting Q1 and Q2.

During initial work, raw milk was diluted in a buffer solution and the cell permeant nucleic acid stain SYTO® 9 was used to stain the bacteria contained in the milk. A flow cytometer, equipped with a 488 nm laser as the light source, forward and right angle scatter detectors, and three fluorescence detectors, was used to detect the fluorescence from labeled bacteria. The three fluorescence detectors in the flow cytometer in that initial experiment had the following optical filters; 527 nm Bandpass (FL1), 590 nm Bandpass (FL2), and a 630 nm Longpass (FL3). The flow cytometer utilizes a system that provides volumetric measurement of the sample analyzed and yields a count per unit volume. When raw milk, to which bacteria were spiked, was diluted in saline buffer and stained with SYTO® 9 the fluorescence signals detected by the flow cytometer was identical to the fluorescence detected in raw milk without spiked bacteria. The conclusion was that the background fluorescent signal from the various components in raw milk, and the non-specific binding of the dye to these components, dominated the signal such that it was impossible to detect any bacteria-related fluorescence. Additionally the large scatter signals detected in flow cytometry from the milk fat globules, casein micelles and other components in the milk, prevented the use of forward and right angle scatter in the detection of bacteria. To prevent the background signal, the inventors of the present invention made an attempt to minimize such interference. This involved the exploration of various chemical and physical treatment of the raw milk as well as various nucleic acid dyes to stain the bacteria. Various enzymes were investigated for their ability to breakdown proteins in milk while preserving the bacteria sufficiently intact for the DNA to remain within the cell structure. Various temperatures, buffering agents, and pH ranges were investigated to optimize the penetration of the otherwise cell-impermeant nucleic acid dyes, thereby improving the bacterial staining with the nucleic acid dye. Sonication of the sample was also investigated as an aid to the enzymatic digestion of various components in the raw milk and to improve bacterial staining.

Staining Composition

The staining composition used in the method of the present invention comprises a buffering agent and a dimeric nucleic acid dye, wherein the dimeric nucleic acid has the formula Q1-BRIDGE-Q2, wherein Q1 and Q2 are nucleic acid dye moieties and BRIDGE is connecting Q1 and Q2. In one embodiment, the staining composition further comprises a protease, such as a serine endopeptidase. The different components of the staining composition are described in more detail in the below.

Dimeric Nucleic Acid Dye

It was found to be important for the present invention, that the staining composition used comprises a particular type of nucleic acid dye, as the present inventors have found that of the nucleic acid dyes tested herein, only nucleic acid dyes having the formula Q1-BRIDGE-Q2, wherein Q1 and Q2 are nucleic acid dye moieties and BRIDGE is connecting Q1 and Q2 showed good performance when used in the method of the invention. A dimeric nucleic acid dye used in the staining composition of the present invention may comprise a pair of identical fluorescent monomeric nucleic acid dye moieties. When Q1 and Q2 are the same, the resulting nucleic acid dye is a homodimer. When Q1 and Q2 are different, the resulting dimer is a heterodimer. Preferably, the dimeric nucleic acid dye used in the staining composition of the present invention is a homodimer. The commercially available nucleic acid dyes GelGreen™, EvaGreen® and GelRed™ are covered by U.S. Pat. Nos. 7,601,498 and 7,803,943, which are incorporated herein by reference.

These dyes were developed for use in staining double stranded DNA and single stranded DNA or RNA in agarose gels in a safe way by replacing cell-permeant and mutagenic known dyes such as Ethidium Bromide, but not for staining and/or counting (living) cells. They were furthermore designed to have low toxicity, superior sensitivity and exceptional stability. Having been developed for staining isolated DNA in a safe way, these dyes have been selected such that they are indeed cell-impermeant to human cells at 37° C. according to the safety sheets of these products. The test described in the safety sheets of these products comprises the following steps:

incubating HeLa cells with the nucleic acid dye in question for 30 minutes at 37° C. at a dye concentration that would be suitable for staining DNA in an agarose gel, performing fluorescence microscopy using optical filter sets appropriate for the dye in question to detect staining of the cells.

Accordingly, as used herein, a nucleic acid dye is "cell-impermeant" if it does not penetrate HeLa cells as determined by no detectable staining of the HeLa cells after 30 minutes of incubation at 37° C. and neutral pH followed by fluorescence microscopy using optical filter sets appropriate for the dye in question.

Figure 5:
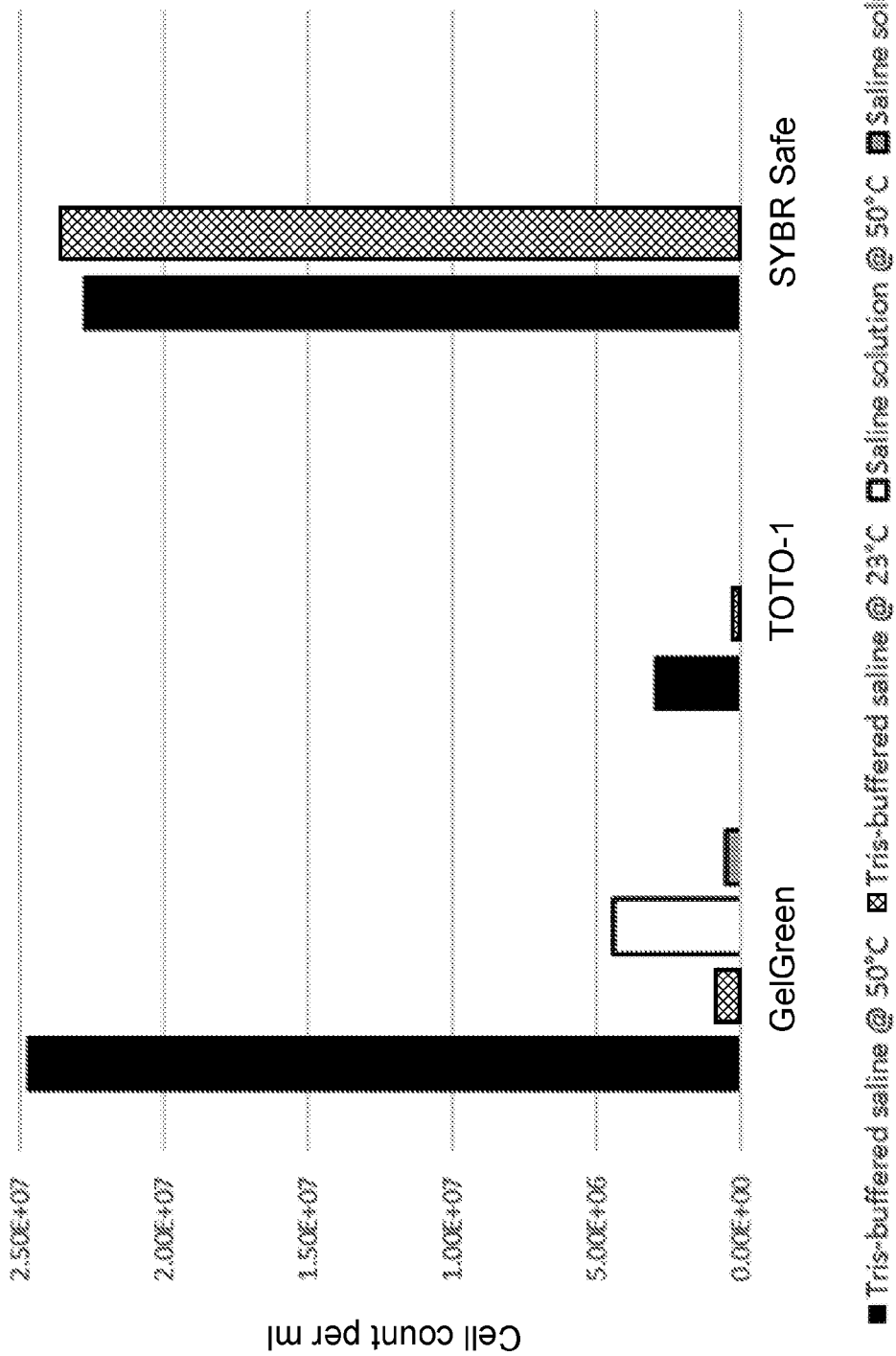
FIG. 5 is a bar diagram showing the ability to stain *E. coli* in different staining compositions using three different dyes and two different heat protocols. The three dyes are Gel-Green™, TOTO®-1 and SYBR® Safe. For GelGreen™ the bars from left to right are 1) Tris-buffered saline (pH8.5) at 50° C., 2) Tris-buffered saline (pH8.5) at 23° C., 3) Saline solution (0.9%) at 50° C. and 4) Saline solution (0.9%) at 23° C. For TOTO®-1 and SYBR® Safe the bars from left to right are 1) Tris-buffered saline (pH8.5) at 50° C. and 2) Tris-buffered saline (pH8.5) at 23° C.

It is very important to note that the chemical structure of these dimeric nucleic acid dyes, such as GelGreen™, were specifically engineered so that the dyes are unable to cross cell membranes under physiological circumstances, thus making them 'cell-impermeant' and thereby not useful for staining whole cells. As such the inventors of the present invention initially selected GelGreen™ to be used as a counterstain in the milk sample with the assumption it would stain other components in the sample, but not the (bacterial) cells. Surprisingly, actual use of the dye in a raw milk sample diluted in a Tris-buffered saline (pH 8.5) at a temperature of approximately 50 to 60° C. resulted in bacterial cells being stained. Further investigation showed that GelGreen™ did not stain bacterial cells at room temperature (23° C.) neither in a saline solution nor in Tris-buffered saline. Furthermore, only minimal staining of bacteria with GelGreen™ appeared at 50° C. in NaCl solution (=saline) (FIG. 5). These results indicates that the combination of temperature, dye, composition of the staining solution and possibly pH is important for obtaining proper staining of the bacteria in raw milk.

The nucleic acid dyes used in the present invention comprises two nucleic acid dye moieties connected by a linker herein referred to as "BRIDGE" thereby forming a dimeric nucleic acid dye. Furthermore, there is a tendency of the two nucleic acid dye moieties to form an intramolecular dimer, primarily H-dimer, which is a particularly useful property in the nucleic acid dye produced. Intramolecular dimer formation may be confirmed by comparing absorption spectra of a dimeric dye in an aqueous solution and absorption spectra of the related monomeric dye or dyes also in an aqueous solution. Any intramolecular dimer formation should cause the spectra of the component monomeric dyes in the dimeric dye to be shifted significantly relative to the spectra of the related monomeric dye(s). In this regard, a significant shift may be about 10 nm or more, by way of example.

Figure 18:
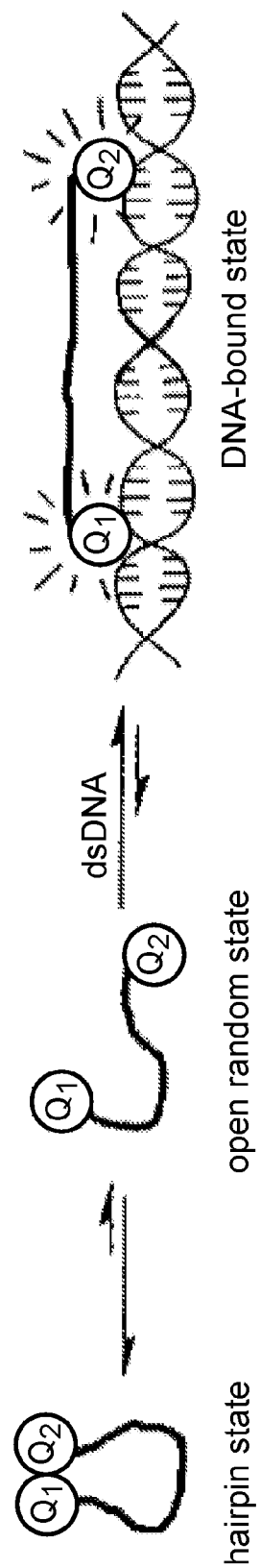
FIG. 18 shows a schematic illustration of the release-on-demand mechanism of the dimeric nucleic acid dyes used in the method of the present invention.
Figure 19:
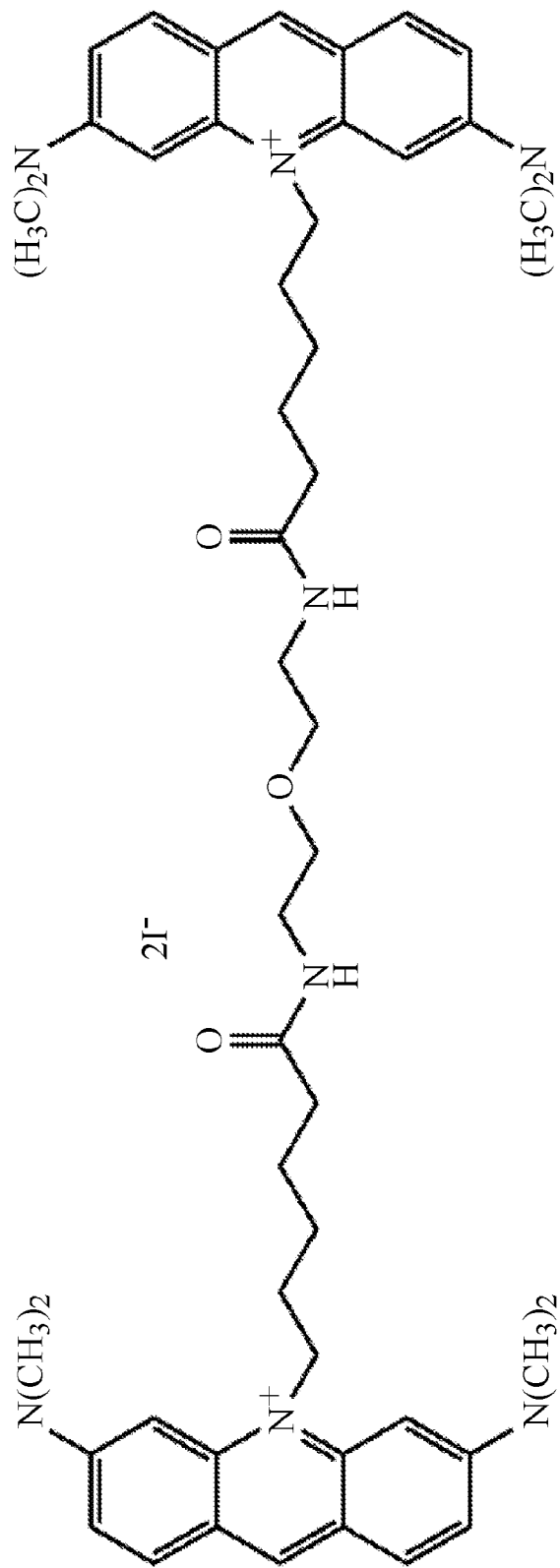
FIG. 19 shows the chemical structure of AOAO-12, which is a dimeric nucleic acid dye wherein Q1 and Q2 are both an acridine-based nucleic acid dye having structure I described herein and are connected with a BRIDGE having the formula —$(CH_2)_5$—C(=O)NH—$(CH_2)_2$—O—$(CH_2)_2$—NH(O=C)—$(CH_2)_5$—.
Figure 20:
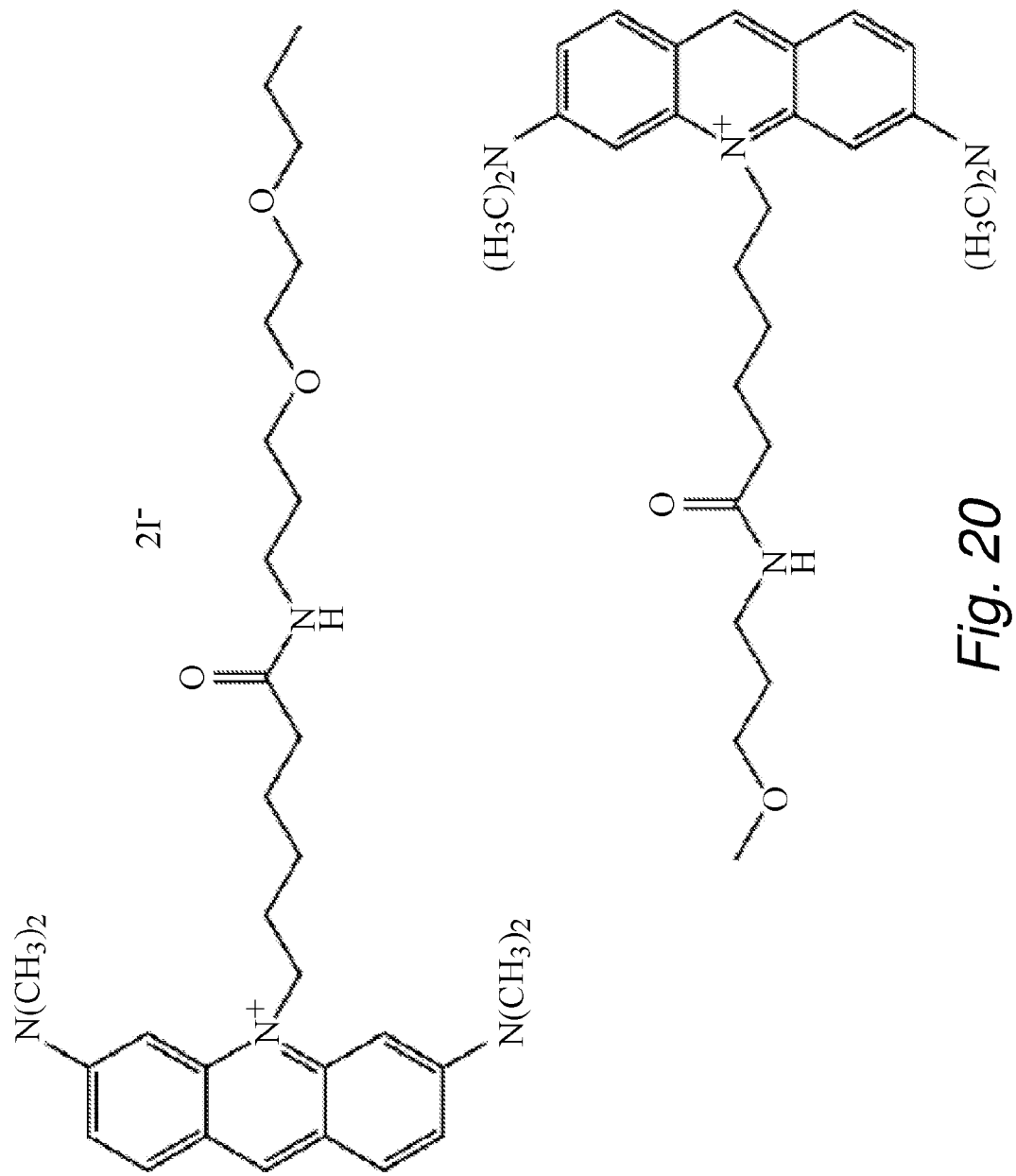
FIG. 20 shows the chemical structure of AOAO-13, which is a dimeric nucleic acid dye wherein Q1 and Q2 are both an acridine-based nucleic acid dye having structure I described herein and are connected with a BRIDGE having the formula —$(CH_2)_5$—C(=O)NH—$(CH_2)_3$—[O—$(CH_2)_2]_2$—O—$(CH_2)_3$—NH(O=C)—$(CH_2)_5$—.
Figure 21:
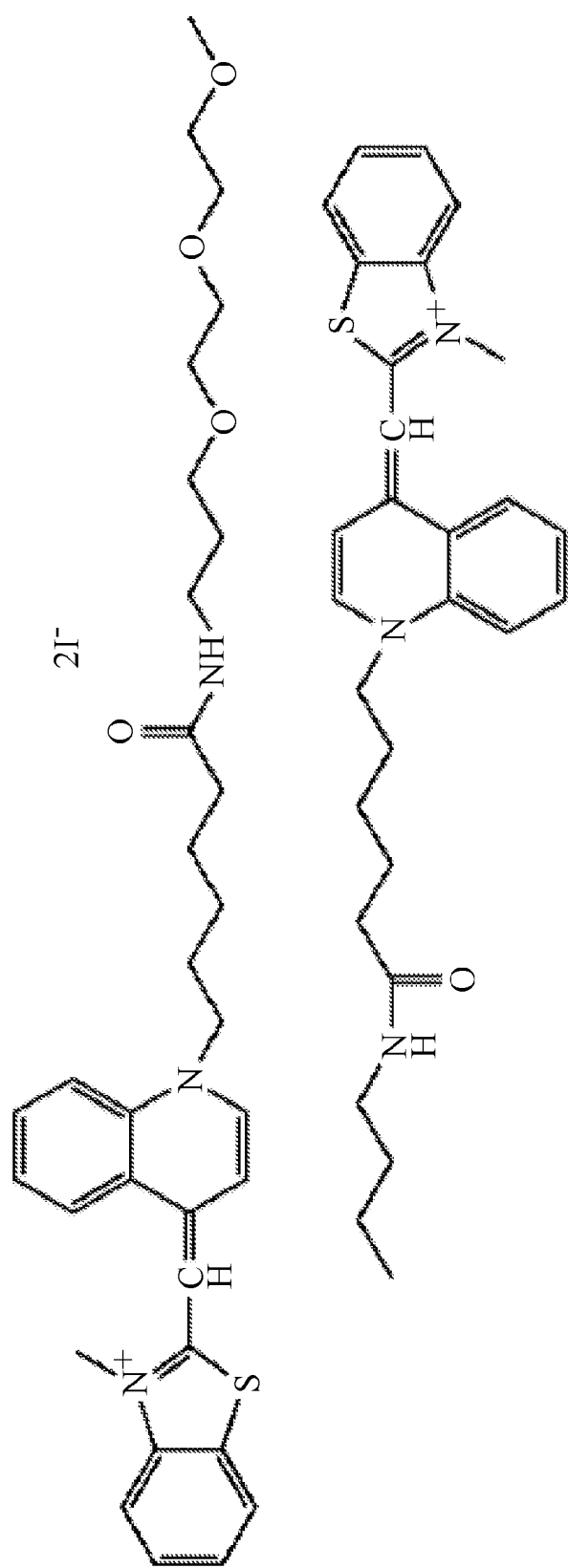
FIG. 21 shows the chemical structure of TOTO-13, which is a dimeric nucleic acid dye wherein Q1 and Q2 are both a an asymmetric cyanine-based nucleic acid dye having structure II described herein and are connected with a BRIDGE having the formula —$(CH_2)_5$—C(=O)NH—$(CH_2)_3$—[O—$(CH2)_2]_2$-O—$(CH_2)_3$—NH(O=C)-$(CH_2)_5$—.
Figure 22:
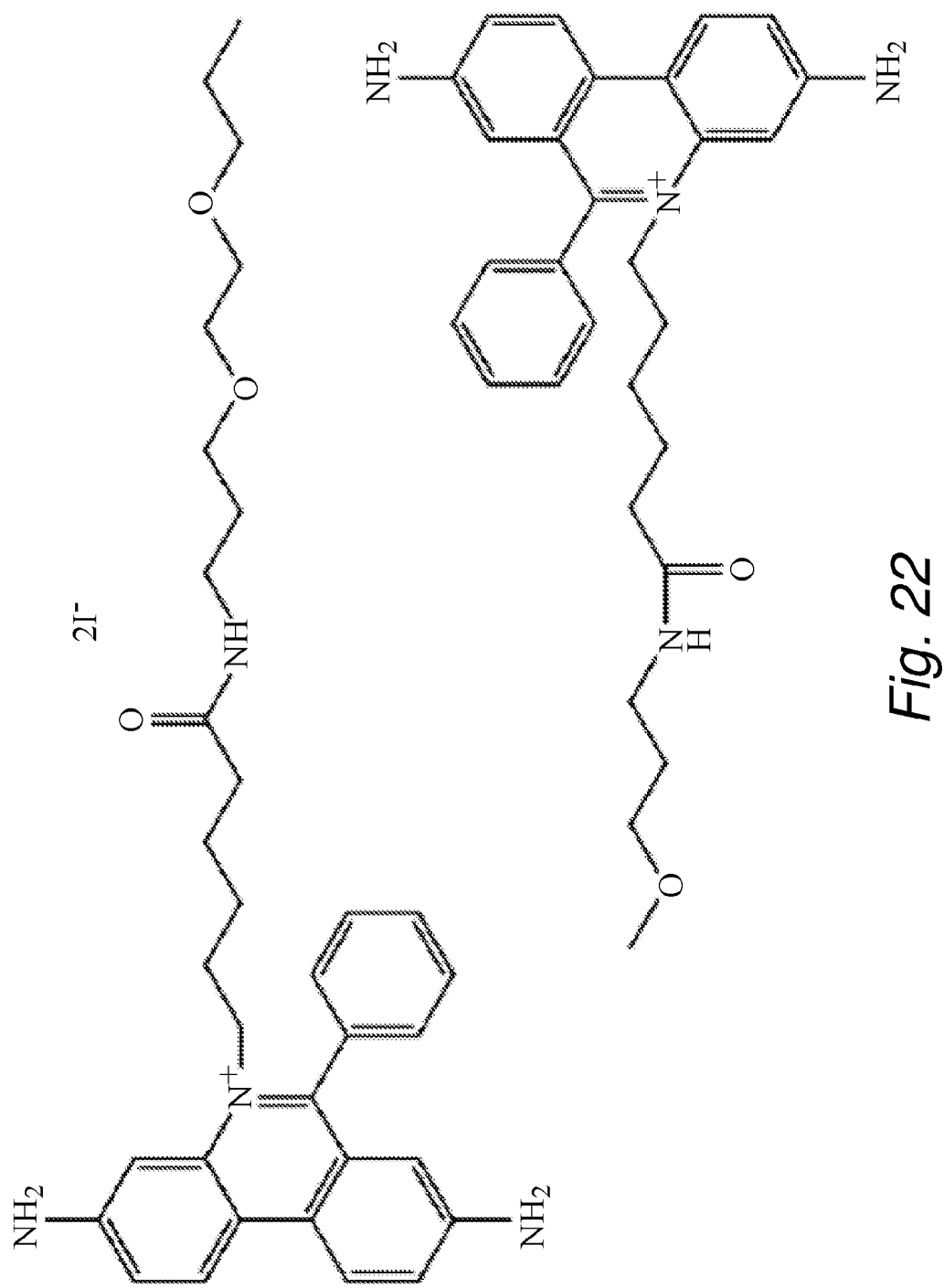
FIG. 22 shows the chemical structure of ET-27, which is a dimeric nucleic acid dye wherein Q1 and Q2 are both a phenanthridinium-based nucleic acid dye having structure III described herein and are connected with a BRIDGE having the formula —$(CH_2)_5$—C(=O)NH—$(CH_2)_3$—[O—$(CH2)_2]_2$-O—$(CH_2)_3$—NH(O=C)—$(CH_2)_5$—.

Due to this intra-molecular dimer formation, the dimeric nucleic acid dyes used in the method of the present invention assumes a predominantly hairpin-like conformation when in solution. This hairpin-like conformation or state of the dye is inactive with respect to nucleic acids, or incapable of interacting or groove-binding with nucleic acids. It is believed that the dye, when in solution and in the presence of nucleic acids, also assumes an open random conformation or state, which exists in small quantity and in substantial equilibrium with the hairpin conformation. The open random conformation or state of the dye is active with respect to nucleic acids, or capable of interacting or binding with nucleic acids. It is believed that when the dye is in the presence of an increasing amount of nucleic acids, an equilibrium shift from the hairpin state toward the intermediate, open random state, or DNA-binding state, occurs. It is believed that this mechanism, sometimes referred to as a "release-on-demand DNA-binding mechanism," reduces background fluorescence and sometimes may also reduce the toxicity of the dye. The dimeric nucleic acid dyes used in the present invention are capable of intramolecular dimer formation, or the formation of a hairpin structure. Furthermore, the dimeric nucleic acid dyes used in the present invention are capable of binding to DNA via a release-on-demand mechanism as e.g. described in U.S. Pat. No. 7,601,498. The release-on-demand mechanism is shown in FIG. 18.

The phenomenon of H-dimer formation in connection with certain dyes has been described in West, et al., J. Phys. Chem. (1965); Rohatgi, et al., J. Phys. Chem. (1966); Rohatgi, et al., Chem. Phys. Lett. (1971); and Khairutdinov, et al., J. Phys. Chem. (1997). Formation of an intramolecular H-dimer may be facilitated when BRIDGE is a flexible and neutral or substantially neutral hydrocarbon linker, optionally comprising one or more neutral nucleic-acid-binding-enhancing-groups NABEG(s). H-dimer formation in a dimeric dye may be associated with two major benefits. One of the major benefits is a reduction, sometimes dramatic, in background fluorescence, coupled with a substantial increase in fluorescence upon DNA-binding, as demonstrated by a large gain in the fluorescence signal. The other major benefit is that H-dimer formation in a dimeric dye may significantly reduce the toxicity, particularly mutagenicity, of the dye. In this regard, a significant reduction in mutagenicity may be on the order of at least about 20% relative to EB, as measured using the Ames Test or an equivalent test. It is believed that reduced mutagenicity may be at least partly attributable to reductions in the cell membrane-permeability and the effective concentration of the dye. Furthermore, the molecular weight of a dimeric nucleic acid dye is generally substantially or significantly larger, such as about two times larger, for example, than the molecular weights of known nucleic acid gel stains. Generally, a molecule having a larger molecular weight has more difficulty penetrating cell membranes than a molecule having a smaller molecular weight. Indeed, the dimeric nucleic acid dyes to be used in the method of the present invention are cell-impermeant.

In a dimeric nucleic acid dye with the formula Q1-BRIDGE-Q2 used in the method of the present invention, BRIDGE is covalently attached to Q1 and Q2. The BRIDGE component of the nucleic acid dyes used in the method of the present invention is a substantially aliphatic comprising from about 8 to about 150 non-hydrogen atoms, such as from about from about 10 to about 100, from about 15 to about 80 or from about 20 to about 50 non-hydrogen atoms. BRIDGE may be positively charged to a relatively limited extent or substantially neutral in charge, and is a substantially flexible constituent that facilitates intramolecular dimer formation to produce a dimeric dye. The constituents of BRIDGE may be selected to provide such limited positive charge or substantial neutrality. The property of substantial neutrality, which includes actual neutrality, is discussed further below. The property of substantial flexibility is generally related to the substantially aliphatic nature, which includes actual aliphatic nature, of BRIDGE. This substantial aliphatic nature generally refers to the non-aromaticity of BRIDGE, or non-rigidity of BRIDGE.

BRIDGE may incorporate at least one independent nucleic-acid-binding-enhancing-group (NABEG). A NABEG is a moiety capable of binding to nucleic acids in the form of electrostatic, hydrophobic, or hydrogen-bonding interactions. Merely by way of example, a NABEG may be selected from primary amines: secondary amines; tertiary amines; ammoniums; amidines; aryl groups optionally comprising hetero atoms selected from N, O, S, and any combination thereof; moieties having bonds comprising hetero atoms of high electronegativity; and any combination thereof. Primary, secondary and tertiary amines and amidines are basic groups and therefore are positively charged or at least partially positively charged at physiological pH. Ammonium groups, or quaternized nitrogen groups, are permanently positively charged. Generally speaking, positively charged or partially positively charged groups enhance the nucleic acid binding of the dye via electrostatic interaction, a property that may be exploited in the development of highly sensitive fluorescent nucleic acid stains. It is generally undesirable to use BRIDGE having excessive positive charges to produce a dimeric dye. A suitable BRIDGE of a dimeric dye may comprise no more than one positive charge. BRIDGE may be a substantially flexible and neutral or substantially neutral linker. In this context, substantially neutrality refers to slight charge. By way of example, BRIDGE could comprise a weakly basic constituent, such as a pyridine group or a pyrazine group, for example, such that when it is in aqueous solution, a very small amount of positive charges may be present. Further by way of example, in a case in which BRIDGE comprises at least one neutral NABEG, the exact amount of positive charge is generally related to the pKa of the NABEG. Generally, the higher the pKa of the NABEG, the more likely the NABEG is protonated and thus, positively charged. By way of example, a suitable weakly basic NABEG group may have a pKa of about 11 or less, such as about 8 or less, or about 7 or less.

In one embodiment BRIDGE has the formula (Formula 1) set forth directly below:

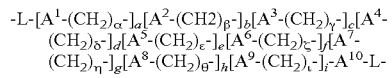

In Formula 2, each L is part of BRIDGE and is covalently linked to Q1 or Q2. Each L is independently a moiety comprising a single bond; a polymethylene unit having 1 carbon to about 12 carbons, optionally comprising at least one hetero atom selected from N, O and S; or an aryl group optionally comprising at least one hetero atom selected from N, O and S. The subscripts associated with the (CH2) methylene units, namely, $\alpha$, $\beta$, $\gamma$, $\delta$, $\epsilon$, $\zeta$, $\eta$, $\theta$, and $\iota$, may be the same or different, each independently indicating the size of the associated methylene unit and, independently, being zero or an integer from 1 to about 20, inclusive, or from 1 to about 12. The subscripts associated with the bracketed portions of Formula 2, namely, a, b, c, d, e, f, g, h, and i, may be the same or different, each independently indicating the size of the associated bracketed portion of the formula and, independently, being zero or an integer from 1 to about 20, such as from 1 to about 10, or from 1 to about 5. $A^1$, $A^2$, $A^3$, $A^4$, $A^5$, $A^6$, $A^7$, $A^8$, $A^9$ and $A^{10}$ may be the same or different, each, independently, being a nucleic-acid-binding-enhancing-group (NABEG); a branched alkyl optionally comprising at least one hetero atom selected from N, O and S; or at least one saturated 5- or 6-membered ring optionally comprising at least one hetero atom selected from N, O and S. $A^1$, $A^2$, $A^3$, $A^4$, $A^5$, $A^6$, $A^7$, $A^8$, $A^9$ and $A^{10}$ may be such that BRIDGE comprises at most one positive charge, or is substantially neutral, and in the latter case, each of these constituents, independently, may itself be substantially neutral, which includes actual neutrality. NABEGs may be selected from moieties comprising at least one bond linkage that comprises at least one hetero atom of high electronegativity or S; and aryl groups optionally comprising at least one hetero atom selected from halogens, N, O, and S. Examples of moieties comprising at least one bond linkage that comprises at least one hetero atom of high electronegativity or S include, but are not limited to moieties comprising at least one amide bond, urethane bond, urea bond, thiourea bond, ether bond, or thioether bond. $A^1$, $A^2$, $A^3$, $A^4$, $A^5$, $A^6$, $A^7$, $A^8$, $A^9$ and $A^{10}$, which may be the same or different, may, independently, be NABEGs selected from moieties comprising at least one bond linkage that comprises at least one hetero atom of high electronegativity or S; and aryl groups optionally comprising at least one hetero atom selected from halogens, N, O, and S. Examples of moieties comprising at least one bond linkage that comprises at least one hetero atom of high electronegativity or S include, but are not limited to moieties comprising at least one amide bond, urethane bond, urea bond, thiourea bond, ether bond, or thioether bond. $A^1$, $A^2$, $A^3$, $A^4$, $A^5$, $A^6$, $A^7$, $A^8$, $A^9$ and $A^{10}$ may be such that BRIDGE comprises at most one positive charge, or is substantially neutral, and in the latter case, each of these constituents may itself be substantially neutral, which includes actual neutrality. BRIDGE may comprise any suitable number of non-hydrogen atoms, as previously described, such as e.g. from about 10 to about 100 non-hydrogen atoms.

Accordingly, in one embodiment, BRIDGE has the formula (formula 1) set forth directly below:

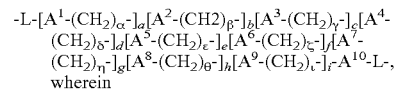

each L is part of BRIDGE and is covalently linked to Q1 or Q2 and is independently a moiety comprising a single bond; a polymethylene unit having from 1 carbon atoms to about 12 carbon atoms and optionally comprises at least one hetero atom selected from N, O and S or an aryl group optionally comprising at least one hetero atom selected from N, O and S, $\alpha$, $\beta$, $\gamma$, $\delta$, $\epsilon$, $\zeta$, $\eta$, $\theta$, and $\iota$, are independently zero or an integer from 1 to about 20, a, b, c, d, e, f, g, h, and i, are independently zero or an integer from 1 to about 20, A1, A2, A3, A4, A5, A6, A7, A8, A9 and A10 are independently selected from the group consisting of a nucleic-acid-binding-enhancing-group, a branched alkyl optionally comprising at least one hetero atom selected from N, O and S and at least one saturated 5- or 6-membered ring optionally comprising at least one hetero atom selected from N, O and S.

Preferably, BRIDGE may have the formula (Formula 2) set forth directly below:

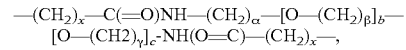

wherein
each L of BRIDGE is —$(CH2)_x$-, where each x, independently, is an integer selected from 1 to 11,
$\alpha$ may be an integer selected from 2 to about 20,
$\beta$ and $\gamma$, are independently zero, 2 or 3,
b is zero or an integer selected from 1 to about 20, and
c is zero, 1 or 2.

More preferably, BRIDGE may have the formula (formula 3) set forth directly below:

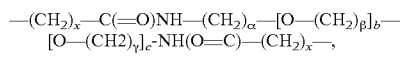
—(CH2)$_x$—C(=O)NH—(CH$_2$)$_\alpha$—[O—(CH$_2$)$_\beta$]$_b$—[O—(CH2)$_\gamma$]$_c$-NH(O=C)—(CH$_2$)$_x$—, wherein
each L of BRIDGE is —(CH2)$_x$-, where each x is 5,
α is 2 or 3,
β is 2,
b is 1 or 2
c is zero, 1 or 2, and
γ is 3, when c is 1 or 2.

In a highly preferred embodiment, BRIDGE has a formula selected from the group consisting of:

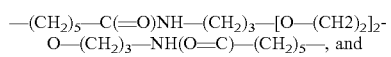
—(CH$_2$)$_5$—C(=O)NH—(CH$_2$)$_3$—[O—(CH2)$_2$]$_2$-O—(CH$_2$)$_3$—NH(O=C)—(CH$_2$)$_5$—, and    a)

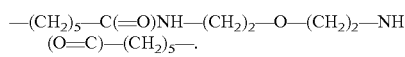
—(CH$_2$)$_5$—C(=O)NH—(CH$_2$)$_2$—O—(CH$_2$)$_2$—NH(O=C)—(CH$_2$)$_5$—.    b)

In a dimeric nucleic acid dye with the formula Q1-BRIDGE-Q2 used in the method of the present invention, Q1 is a nucleic acid dye moiety, Q2 is a nucleic acid dye moiety and Q1 and Q2 may be the same or different. Preferably, Q1 and Q2 are the same. As used herein, the term "dye" refers to an aromatic molecule capable of absorbing light in the spectral range of from about 250 nm to about 1,200 nm. Generally, the term "dye" may refer to a fluorescent dye, a non-fluorescent dye, or both. Generally, the term "fluorescent dye" refers to a dye capable of emitting light when excited by another light of appropriate wavelength. As used herein, the term "nucleic acid dye" refers to a dye capable of binding to a nucleic acid to form a dye-nucleic acid complex. As used herein, the term "nucleic acid dye moiety" refers to the functional group of a nucleic acid dye in a molecule, which molecule in the case of the dimeric nucleic acid dyes of the present invention has the formula Q1-BRIDGE-Q2. In a preferred embodiment, the nucleic acid dye moiety is fluorescent. A "fluorescent nucleic acid dye" refers to a dye capable of binding to a nucleic acid to form a fluorescent dye-nucleic acid complex. A fluorescent nucleic acid dye is typically non-fluorescent or weakly fluorescent by itself, but becomes highly fluorescent upon nucleic acid binding.

In a preferred embodiment the dimeric nucleic acid dye used in the staining composition of the present invention comprises a fluorescent nucleic acid dye moiety Q1 and a fluorescent nucleic acid dye Q2, wherein Q1 and Q2 may be the same, or different. Method according to any of the preceding claims, wherein Q1 and/or Q2 is a fluorescent nucleic acid dye moiety. Q1 and Q2 may independently be fluorescent nucleic acid dye moieties each derived from a nucleic acid dye selected from the group consisting of an acridine-based nucleic acid dye, an asymmetric cyanine-based nucleic acid dye, a phenanthridinium-based nucleic acid dye, a symmetric cyanine-based nucleic acid dye, a pyronin nucleic acid dye, a styryl nucleic acid dye, a derivative of DAPI, and a derivative of a Hoechst dye. DAPI and Hoechst dyes generally cannot be directly attached to BRIDGE because they do not possess a reactive group for bond formation. In this context, a derivative refers to a base dye, such as DAPI or a Hoechst dye, that is modified sufficiently for bond formation, such as by addition of a reactive group. Preferably, the fluorescent nucleic acid dye moiety is derived from a nucleic acid dye selected from the group consisting of an acridine-based nucleic acid dye, an asymmetric cyanine-based nucleic acid dye and a phenanthridinium nucleic acid dye. Preferably Q1 and Q2 are the same fluorescent nucleic acid dye moiety.

The dimeric nucleic acid dyes used in the method of the present invention may be associated with an anion that balances positive charge(s) associated with the dye. Such anion may be biologically compatible. Examples of a suitable anion include, but are not limited to, a halide, a sulfate, a phosphate, a perchlorate, a tetrafluoroborate, and a hexafluorophosphate. Merely by way of example, the anion may be chloride or iodide.

When the fluorescent nucleic acid dye moiety is an acridine-based nucleic acid dye it preferably has the structure (structure I) set forth directly below:

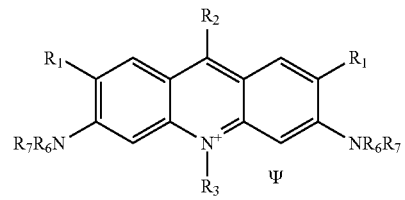

wherein,
each R1 is independently selected from the group consisting of H, a C1-C2 group, and an alkyl,
BRIDGE is attached to R2 or R3,
when BRIDGE is attached to R2, R3 is selected from the group consisting of H or —CH3,
when BRIDGE is attached to R3, R2 is selected from the group consisting of H, —CH3, —NH2, —NHCH3, —CN, and —C(=O)NH2,
each of R6 and R7 is independently selected from the group consisting of H, a C1-C2 group and an alkyl, and
ψ is an anion that balances positive charge(s) associated with the dye, When the fluorescent nucleic acid dye moiety is an asymmetric cyanine-based nucleic acid dye it preferably has the structure (structure II) set forth directly below:

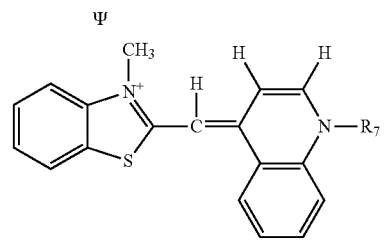

wherein,
BRIDGE is attached to R7, and
ψ is an anion that balances positive charge(s) associated with the dye.

When the fluorescent nucleic acid dye moiety is phenanthridinium-based nucleic acid dye it preferably has the structure (structure III) set forth directly below:

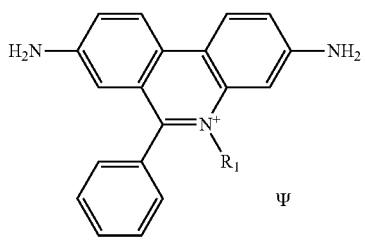

wherein,
BRIDGE is attached to R1, and
ψ is an anion that balances positive charge(s) associated with the dye.

In a highly preferred embodiment of the present invention, the dimeric nucleic acid dye is selected from the group consisting of:
a) A dimeric nucleic acid dye, wherein Q1 and Q2 are both a fluorescent nucleic acid dye moiety having the structure of structure I set forth in the above and are connected by a BRIDGE of the formula —$(CH_2)_5$—C(═O)NH—$(CH_2)_3$—[O—$(CH2)_2$]$_2$-O—$(CH_2)_3$—NH(O═C)—$(CH_2)_5$—
b) A dimeric nucleic acid dye, wherein Q1 and Q2 are both a fluorescent nucleic acid dye moiety having the structure of structure I set forth in the above and are connected by a BRIDGE of the formula —$(CH_2)_5$—C(═O)NH—$(CH_2)_2$—O—$(CH_2)_2$—NH(O═C)—$(CH_2)_5$—,
c) A dimeric nucleic acid dye, wherein Q1 and Q2 are both a fluorescent nucleic acid dye moiety having the structure of structure II set forth in the above and are connected by a BRIDGE of the formula —$(CH_2)_5$—C(═O)NH—$(CH_2)_3$—[O—$(CH2)_2$]$_2$-O—$(CH_2)_3$—NH(O═C)—$(CH_2)_5$—, and
d) A dimeric nucleic acid dye, wherein Q1 and Q2 are both a fluorescent nucleic acid dye moiety having the structure of structure III set forth in the above and are connected by a BRIDGE of the formula —$(CH_2)_5$—C(═O)NH—$(CH_2)_3$—[O—$(CH2)_2$]$_2$-O—$(CH_2)_3$—NH(O═C)—$(CH_2)_5$—.

In another highly preferred embodiment, the dimeric nucleic acid dye used in the staining composition of the present invention has a chemical structure selected from the group consisting of structure IV, V, VI and VII shown in FIGS. 19, 20, 21 and 22, respectively. While the structures shown in FIGS. 19, 20, 21 and 22 show two iodide anions, any other appropriate anions, such as those described herein may be used in place of the iodide anions shown.

Dimeric nucleic acid dyes that are cell-impermeant and which binds to DNA via a release-on-demand mechanism and which have the formula Q1-BRIDGE-Q2 in accordance with the above of description are commercially available from Biotium as GelGreen™, EvaGreen® and GelRed™. Furthermore, they can be prepared as described in the relevant examples of U.S. Pat. Nos. 7,601,498 and 7,803,943, which examples are hereby incorporated by reference.

Based on the teaching of the present invention, the skilled person will realize that a suitable concentration of the dimeric nucleic acid dye in the staining composition may vary depending on the dye used and the cells to be counted. As a general rule, the present invention works well when using a staining composition comprising the dimeric nucleic acid dye in a concentration in the same range as the concentration the same dye would be used in for staining of DNA in an agarose gel, such as at approximately the same concentration as the same dye would be used in for staining of DNA in an agarose gel.

Buffering Agents

It was also found to be important for the present invention that the staining composition used further comprises a buffering agent. The buffering agent is preferably an organic buffering agent, and more preferably the buffering agent comprises an amine, such as a primary or secondary amine. In a preferred embodiment the buffering agent is selected from the group consisting of Tris (tris(hydroxymethyl)aminomethane) and CAPS (N-cyclohexyl-3-aminopropanesulfonic acid). In a highly preferred embodiment, the buffering agent is Tris. In a preferred embodiment, the buffering agent is present in the staining composition in a concentration from about 10 to about 500 mM, such as from about 20 to about 400 mM, from about 40 to about 300 mM, from about 60 to about 400 mM, from about 80 to about 300 mM or from about 100 to about 200 mM.

The staining composition used in the method of the present invention preferably has a pH from about 8 to about 11.5, such as from about 8 to about 11, from about 8 to about 10.6, from about 8.5 to about 10.6 at room temperature, i.e. prior to raising the temperature either during the optional preheating of the staining composition or during the incubation with the sample. It is known that pH is dependent on temperature. Whenever referral is made to a pH setting (as in a pH range from 8 to 10.6 as often used herein), such buffers with such pH were prepared at room temperature (–25° C.), unless otherwise stated. The pH may decrease when the final temperature during which the staining reaction is performed is increased, for instance to the preferred temperature ranges as disclosed herein. However, generally, when Tris is used as the buffering agent and the staining composition has an initial pH of around 9.5 at room temperature (RT), pH will decrease to a range between 8 and 8.5 when held at temperatures above 60° C. This means that even though the staining composition or the mixture comprising the staining composition or is heated, the pH will in general be within the range of 8 to 10.6 as referred to herein. Due to the decrease in pH upon heating, the present inventors have found that it is not necessary to adjust pH of the staining composition comprising dimeric nucleic acid dye and Tris, in which case the pH is approximately 10.6 at room temperature. As used herein, the terms "Tris-NaCl buffer", "Tris-saline buffer" and "Tris-buffered saline" are used interchangeably and refer to a buffer comprising Tris as the buffering agent and 150 mM NaCl, wherein pH is adjusted by titration with HCl. As used herein, the terms "Tris-NaCl solution" and "Tris-saline solution" are used interchangeably and refer to a solution Tris as the buffering agent and 150 mM NaCl, but wherein pH has not been adjusted but is approximately 10.6. As used herein, the term "saline solution" and "NaCl solution" are used interchangeably and refer to a 150 mM NaCl solution. 150 mM NaCl corresponds to a 0.9% NaCl solution.

Subjecting bacteria to heat is known to change their permeability (see U.S. Pat. No. 5,410,030). However, it is generally accepted in the art that bacteria then must be subjected to very high temperatures (90° C. or higher) to compromise the membrane sufficiently to allow for complete permeabilization and entry of cell-impermeant dyes. In fact the cell-impermeant dye TOTO®-1 exhibits minimal staining of bacteria when heated to 50° C. in Tris-buffered saline with bacteria (FIG. 5). Compared to TOTO®-1, GelGreen™ unexpectedly exhibits significantly different staining behavior when in Tris-buffered saline at 50° C.

Figure 13:
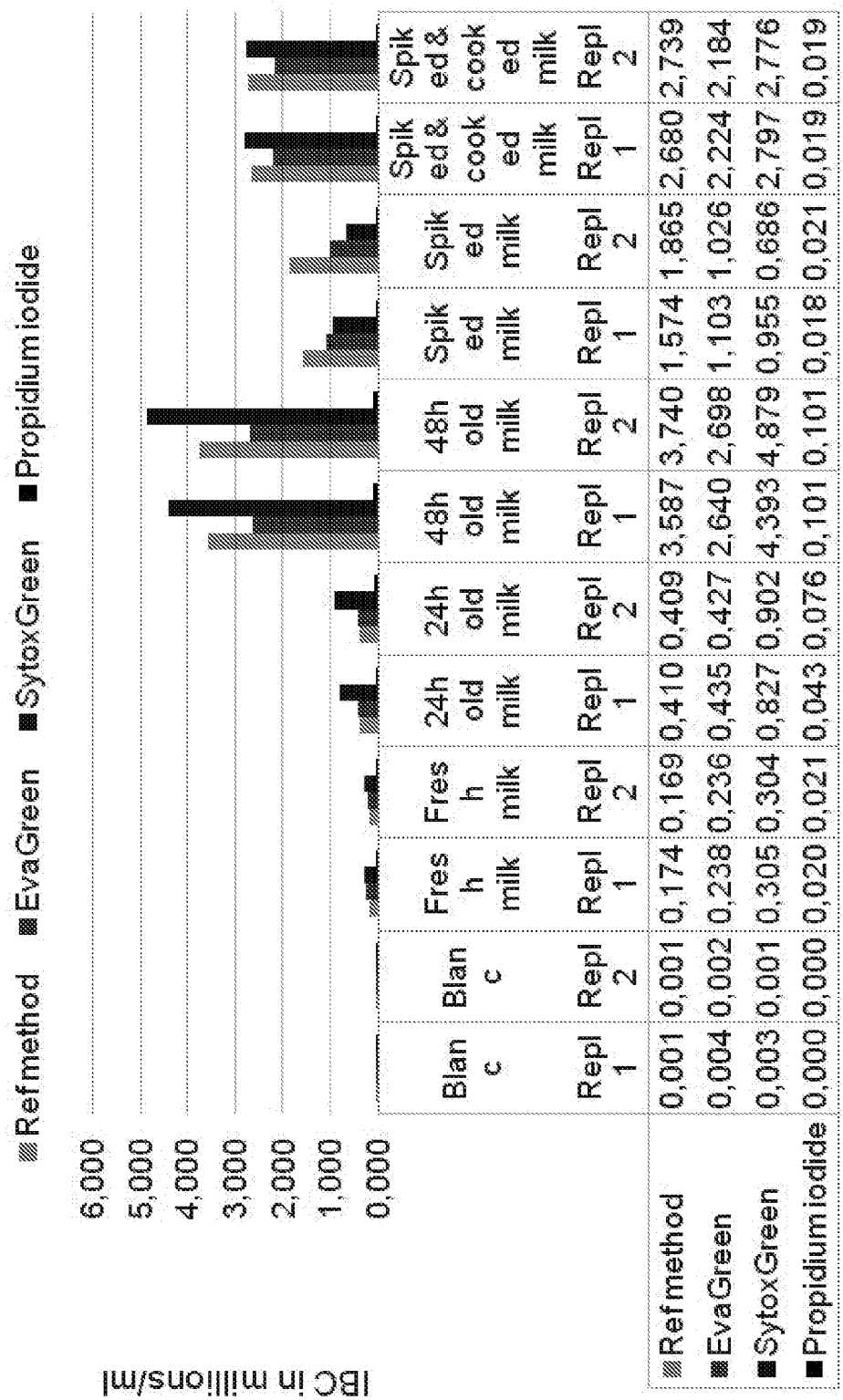
FIG. 13 is a bar diagram of the four tested dyes for each of the tested samples. For each sample the bars from left to right are 1) the reference method (GelGreen™), 2) EvaGreen®, 3) SYTOX® Green and 4) Propidium iodide, "Blanc" is purified water, "Fresh milk" is less than 24 hour old raw fresh milk obtained from local farmer, "24 h milk" is 24 hour old milk obtained from milk factory, "48 h milk" is 48 hour old milk obtained from milk factory, "spiked milk" is raw fresh milk spiked with live *E. coli* and "spiked and cooked milk" is raw fresh milk spiked with cooked (dead) *E. coli*. IBC numbers are given in million counts per ml.

(FIG. 5) and even better performance when temperature was increased to from about 62° C. and to about 68° C. The same conclusion was reached when comparing the staining behavior of the cell-impermeant GelGreen™ and EvaGreen® to cell-impermeant SYTOX® Green (FIG. 13). Accordingly, the method of the present invention works when the staining composition comprises GelGreen™ or EvaGreen®, which are both cell-impermeant dimeric nucleic acid dyes having the formula Q1-BRIDGE-Q2, as opposed to when the staining composition comprises TOTO®-1 or SYTOX® Green. Based on this, it was concluded that it is important for the present invention, to use dimeric nucleic acid dyes having the formula Q1-BRIDGE-Q2 as exemplified with GelGreen™ and EvaGreen® in the staining composition. Although it is preferred to use a staining composition comprising Tris as the buffering agent for staining bacteria using the GelGreen™, other buffering agents also work. Suitable buffering agents to be used in the staining composition are selected from organic biological buffering agents, in particular organic buffering agents comprising an amine, such as preferably Tris or CAPS, most preferably Tris. Furthermore, other cell-impermeant dimeric nucleic acid dyes than GelGreen™ may perform better in another buffer. Finding the correct buffer to obtain optimal staining with a particular dye, based on the current teaching, is something a person of general skill in the art could thus easily perform.

Cells and Samples

The cells to be counted in a liquid sample by the method of the present invention may be all kinds of cells. In a preferred embodiment, said cells are somatic and/or bacterial cells. Preferably, the cells are somatic and/or bacterial as exemplified herein. The somatic cells may for example include Epithelial cells, polymorphonuclear leukocytes (PMNs), macrophages and lymphocytes present in milk. The bacterial cells may include gram positive as well as gram negative cells. The gram positive bacteria may well be selected from the group consisting of *Listeria monocytogenes* (Lm), *Staphylococcus aureus* (Sa) and *Bacillus cereus* (Bc). The gram negative bacteria may well be selected from the group consisting of *Pseudomonas aeruginosa* (Pa) and *Escherichia coil* (Ec).

In a preferred embodiment, the liquid sample is a biological sample selected from the group consisting of milk, blood, urine, saliva, feces and spinal fluid. Especially preferred samples are (cow) milk samples, such as raw milk samples obtained from cattle. From a consumer's and health organization perspective it is beneficial to measure the number of bacterial cells in a milk sample to determine whether the milk is suitable for consumption. From a farmer's or milk producer perspective it is beneficial to also measure the bacterial cells for a similar purpose, but also to measure somatic cells as such would be indicative for mastitis.

In another preferred embodiment, the liquid sample is an environmental sample, such as for example waste water, lake water and soil. The liquid sample can also be other aqueous samples for which it is desired to know the bacterial counts to determine whether it is clean or needs further purification.

When a sample is solid or semi-solid material, e.g. in the case of feces or soil, the solid or semi-solid material is either dispersed or dissolved in water or buffer which is then diluted into the staining composition or it is dispersed or dissolved directly in the staining composition. Either way, the solid or semi-solid sample becomes a liquid sample in which cells can be counted according to the method of the present invention.

Protease

In a preferred embodiment of the present invention, the staining composition further comprises a protease, which is preferably a non-specific protease, more preferably a serine endopeptidase such as subtilisin A (EC 3.4.21.62), such as the commercially available proteases Alcalase® and Savinase®. The enzymes Savinase® and Alcalase® are preferred non-specific proteases to be utilized in the methods of the present invention because their proteolytic activity is capable of decomposing materials in the raw milk sample other than the bacteria in a reasonable short period (less than 10 min with heat, proper pH and preferably sonication). However, other non-specific proteases with a similar enzyme activity to Savinase® or Alcalase® may be used. It is particularly useful that the staining composition comprises a protease, when the cells to be counted are bacterial cells in a biological sample to reduce the noise from the other components in the biological sample. When the staining composition comprises a protease, pH of the staining composition and temperature of the incubation step c) is selected such as to provide a suitable environment for the enzyme's activity, and may be adjusted depending on the type of proteolytic enzyme that is used, using ordinary measures known in the art. The amount of protease used depends on the type of protease and its specific activity. Based on the present disclosure, the skilled person can adjust the amount of protease present in the staining composition so as to reduce the noise from the other material in the sample than the cells to be counted. By way of example, the staining composition used in the method of the present invention may suitably comprise from about 0.1 AU/ml to about $2\times10^3$ enzyme AU/ml (Anson unit/ml), such as, from about 0.12 AU/ml to about $1.92\times10^3$ AU/ml, AU/ml, where AU is defined as is defined as the amount of enzyme that liberates 1.0 μmol (181 μg) tyrosine from casein per minute at pH 7.5 at 37° C.

Sonication

The mixture obtained in step a) and/or the mixture obtained in step c) may optionally be sonicated in order to increase the cell permeability for the nucleic acid dye. In one embodiment, at least one of the optional sonication steps b) or d) are performed. When performed, is important that sonication is performed gently enough to preserve the cells to be counted in the sense of avoiding lysis of said cells. This means that the cells to be counted shall remain sufficiently intact for the DNA to remain with the structure of a cell allowing the DNA-stained cells to be counted. Sonication potentially helps the bacteria cell wall to become permeable and furthermore makes sure that bacteria are not lumped together during the flow cytometric counting. In one embodiment, the somatic and bacterial cells are counted simultaneously and the mixture obtained in step a) and/or the mixture obtained in step c) is sonicated at about 15 to about 50 kHz, such as from about 20 to about 45 kHz, or at about 22.5 kHz to about 40 kHz for about 1 to about 10 seconds, such as from about 2 to about 9, from about 3 to about 8, from about 4 to about 7, from about 5 to about 6 seconds. The mixture of the sample with the staining composition is optionally sonicated for approximately 1 to 10 seconds by either direct placement of the sonicator probe into the sample, or indirectly by placing the appropriate sonicator probe against the cup in which the sample is held; the sample with the staining composition is incubated (preferably in a mixer cup) at a temperature from about 45 to about 95° C., such as from about 47 to about 90° C., from about 50 to about 85° C., from about 52 to about 80° C., from about 57 to about 75° C., from about 60 to about 70°

C., from 61 about to about 69° C. or preferably from about 62 to about 68° C., up to 1 to 2 min; the sample is then optionally again sonicated for approximately 1 to 10 seconds, again either directly or indirectly; before proceeding to the cell counting in step e).

Incubation

The mixture of the staining composition and the sample is incubated in step c) under conditions that renders the cells permeable to the nucleic acid dye. In a preferred embodiment, the incubation is performed at a temperature from about 45 to about 95° C., such as from about 47 to about 90° C., from about 50 to about 85° C., from about 52 to about 80° C., from about 57 to about 75° C., from about 60 to about 70° C., from 61 about to about 69° C. or from about 62 to about 68° C. As already explained in the above, pH during the incubation step will be influenced by the increased temperature and will therefore differ from the pH in the staining composition. Preferably, pH during the incubation step c) is from about 8 to about 11.5, such as from about 8 to about 11, from about 8 to about 10.6, from about 8.5 to about 10.6. The incubation in step c) is suitably performed for less than 10 minutes, such as for less than 9, such as less than 8, 7, 6, 4, 3 or 2 minutes, and preferably for approximately 1 minute. The short incubation time required in step c) while still obtaining a reliable cell count, is a major advantage of the present invention.

Cell Counting

After the incubation step c) and optionally the sonication step d) the stained cells are counted by using fluorescence detecting instrument set to detect the fluorescence of the dimeric nucleic acid dye used. The skilled person is aware of different methods to count stained cells in solution. In a preferred aspect of the present invention, the stained cells are counted by using a fluorescence detecting instrument, such as a flow cytometer, a fluorescence microscope or fluorescent imaging system, a fluorometer or a fluorescence plate reader. The detection of the fluorescence from the labeled cells, such as bacteria, is preferably performed using a flow cytometer (also referred to as FCM).

In one embodiment, somatic and bacterial cells are counted simultaneously.

In a highly preferred embodiment of the invention, a method of staining (and counting) bacteria in raw milk is performed as follows: Savinase® (or Alcalase®) and GelGreen™ are added to a Tris-saline solution (pH 10.6), further referred to as the staining composition; this staining composition is preheated to a temperature of from about 45 to about 95° C., such as from about 47 to about 90° C., from about 50 to about 85° C., from about 52 to about 80° C., from about 57 to about 75° C., from about 60 to about 70° C., from 61 about to about 69° C. or preferably from about 62 to about 68° C.; a small volume of raw milk sample is preheated just long enough for the sample to reach a temperature of from about 45 to about 95° C., such as from about 47 to about 90° C., from about 50 to about 85° C., from about 52 to about 80° C., from about 57 to about 75° C., from about 60 to about 70° C., from 61 about to about 69° C. or preferably from about 62 to about 68° C.; the preheated sample is preferably diluted about 1:10 in the preheated staining composition; the mixture of the sample with the staining composition is optionally sonicated for approximately 5 to 10 seconds by either direct placement of the sonicator probe into the sample, or indirectly by placing the appropriate sonicator probe against the cup in which the sample is held; the sample with the staining composition is incubated (preferably in a mixer cup) at a temperature of from about 45 to about 95° C., such as from about 47 to about 90° C., from about 50 to about 85° C., from about 52 to about 80° C., from about 57 to about 75° C., from about 60 to about 70° C., from 61 about to about 69° C. or preferably from about 62 to about 68° C., up to 1 to 2 min; the sample is then optionally again sonicated for approximately 5 to 10 seconds, again either directly or indirectly; and finally the mixture (or a representative part thereof) is analyzed on the flow cytometer and the fluorescent signals from the somatic cells and/or bacteria are detected and a count per unit volume is determined. This entire procedure from taking the sample to read-out takes less than 10 minutes, and preferably less than 9, 8, 7, 6, 5, 4, 3, 2, or 1 min. In an alternative method, the milk sample itself is not preheated before mixing, but becomes heated when mixed with a preheated staining composition to a temperature that allows optimal entry of the dye into the cells/microorganisms.

In one preferred aspect, said protease and said dimeric nucleic acid dye are mixed in a Tris-buffered saline to form said staining composition. And in yet another preferred embodiment of the present invention, a method is provided according to the invention wherein said staining composition is heated to from about 45 to about 95° C., such as from about 47 to about 90° C., from about 50 to about 85° C., from about 52 to about 80° C., from about 57 to about 75° C., from about 60 to about 70° C., from 61 about to about 69° C. or preferably from about 62 to about 68° C., before it is mixed with said sample. In concert therewith, preferably said sample is heated to from about 45 to about 95° C., such as from about 47 to about 90° C., from about 50 to about 85° C., from about 52 to about 80° C., from about 57 to about 75° C., from about 60 to about 70° C., from 61 about to about 69° C. or preferably from about 62 to about 68° C., when it is mixed with said staining composition. The sample may also be preheated directly before mixing with the staining composition. Depending on the type of sample the skilled person is able to decide whether to preheat or to use a sample at its original temperature before mixing (milk is generally stored in a cold place, or when directly derived from the source such as a cow, the milk may have a temperature that is above storage temperature, but below incubation temperature). When the sample and staining composition are mixed, the incubation takes place at the preferred and optimal temperatures to obtain the most efficient entry of the dye into the cells. Alternatively, the sample is not preheated (and has a cold storage temperature, for instance), but reaches an optimal temperature for dye entry when it is mixed with the preheated staining composition.

In a highly preferred embodiment, the present invention relates to a method of counting cells, such as somatic and/or bacterial cells in milk, such as cow milk, said method comprising the steps of:

a) mixing a staining composition comprising a dimeric nucleic acid dye, a protease and a buffering agent with said milk;

b) optionally sonicating the mixture of step a) for about 1 to about 10 seconds, such as for about 5 seconds at from about 15 to about 50 kHz;

c) incubating the mixture at a temperature from about 62° C. to about 68° C. for about 1 minute to about 5 minutes;

d) optionally sonicating the incubated mixture of step c) for about 1 to about 10 seconds, such as for about 5 seconds at from about 15 to about 50 kHz, and e) counting the cells that are stained with said dye within said mixture, or a part thereof, using a flow cytometer: wherein, the nucleic acid has the formula Q1-BRIDGE-Q2, wherein Q1 and Q2 are nucleic acid dye moieties connected by BRIDGE, Q1 and Q2 are the same and are selected from the group consisting of nucleic acid dye moieties having structure I, structure II and structure wherein BRIDGE has a formula selected from the group consisting of

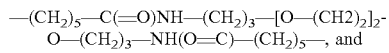

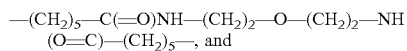

the buffering agent is Tris.

In this embodiment, it is preferred that at least one of the optional sonication steps b) or d) are performed and even more preferred that both of the sonication steps are performed. The protease is preferably a serine endopeptidase (EC 3.4.21.62). Preferably, the protease is used in an amount of from about 0.1 AU/ml to about $2 \times 10^3$ enzyme (Anson unit/ml), such as, from about 0.12 AU/ml to about $1.92 \times 10^3$ AU/ml. It is also preferred that the staining composition comprises Tris in a concentration from about 10 to about 500 mM, such as from about 20 to about 400 mM, from about 40 to about 300 mM, from about 60 to about 400 mM, from about 80 to about 300 mM or from about 100 to about 200 mM.

The invention furthermore relates to a method of making a staining composition comprising a dimeric nucleic acid dye, said method comprising the steps of maintaining said dye at a pH of 8 to 11 in a suitable buffer and heating said dye in said buffer to a temperature of from about 45 to about 95° C., such as from about 47 to about 90° C., from about 50 to about 85° C., from about 52 to about 80° C., from about 57 to about 75° C., from about 60 to about 70° C., from 61 about to about 69° C. or preferably from about 62 to about 68° C.

One of the advantages of the method of the present invention is that it does not require the use of an ion-chelating agent, a detergent, or a centrifugation step to process a liquid sample, such as a milk. Rather it uses a combination of heat, enzymatic treatment and sonication in an appropriate buffer with a nucleic acid stain, to both diminish interfering fluorescence signals from materials in the liquid sample while specifically staining the somatic cells and/or bacteria, making this a relatively simple and rapid method, taking less than 10 minutes per sample from sampling to read-out, such as less than 9, 8, 7, 6, 5, 4, 3 or 2 minutes. Furthermore, as explained for the used apparatus to perform the analysis, multiple samples can sequentially be measured inside the machine. The method applies certain pH and temperature ranges, and optionally sonication, and a proteolytic enzyme to breakdown the interfering materials in the sample while preserving and labeling (staining) the bacteria. No centrifugation or use of toxic compounds is required. Moreover, also no detergents or ion-chelating agents are required.

Another advantage is that the method of the present invention uses a dimeric nucleic acid dye that under normal circumstances is safe as it does not penetrate eukaryotic or prokaryotic cells at 37° C. and therefore also not at room temperature. In other words, the present invention provides a method for using cell-impermeant, non-mutagenic nucleic acid dyes that do not normally cross the membranes of living cells, such as GelGreen™ or GelRed™ to stain the somatic cells and/or bacteria, thus providing a novel staining method and an environmentally safer staining material.

Yet another advantage of the present invention is that it relates to a method that is fast and that requires only a few steps. The present invention is especially suitable for high-throughput measurements.

Figure 7:
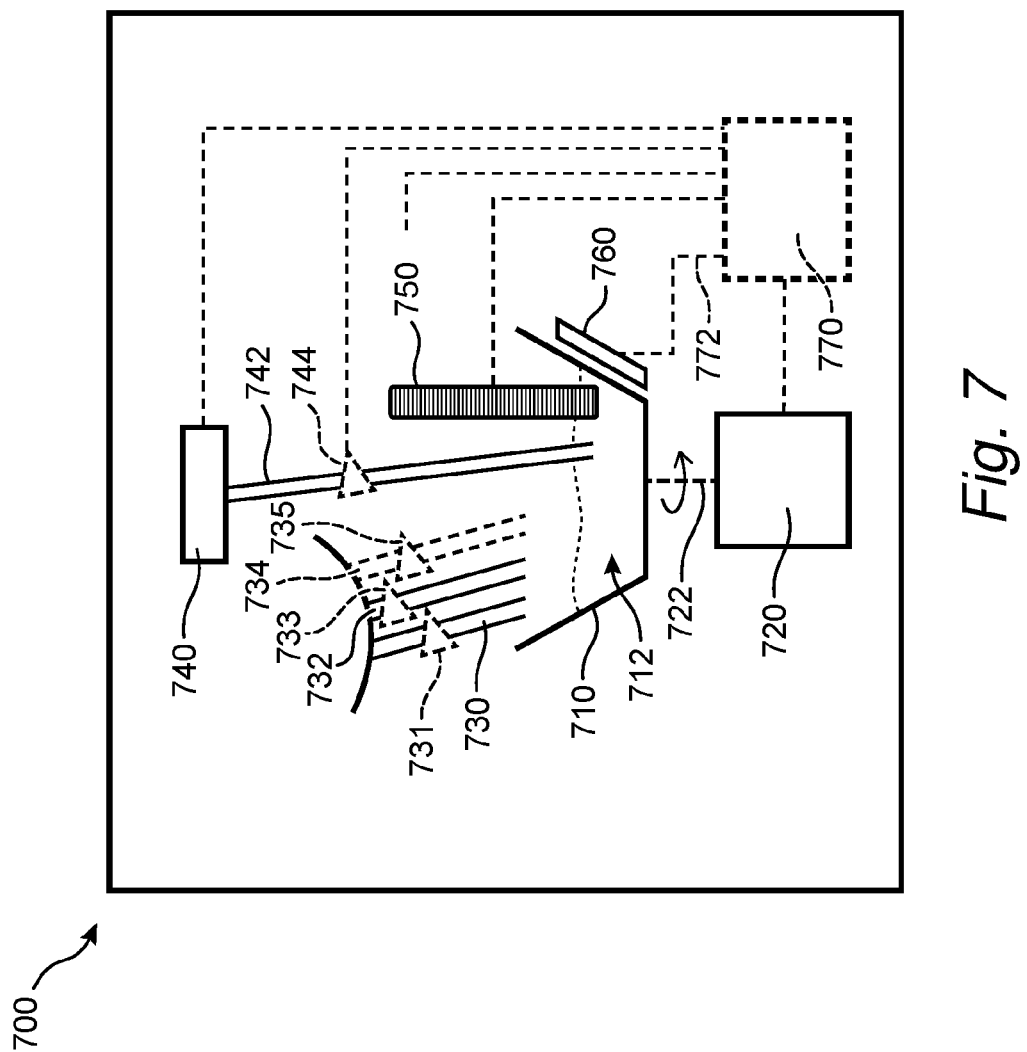
FIG. 7 schematically shows an apparatus for counting cells in a liquid sample.

FIG. 7 schematically shows an apparatus 700 for counting cells in a liquid sample. The apparatus 700 is for performing the previously discussed method of counting cells in a liquid sample. The apparatus 700 comprises a mixing cup 710, a motor 720, a heating element 760, an optional sonicator 750, a sample inlet 730, a staining composition inlet 732, an outlet 742, a measurement module 740, and an optional controller 770. Optionally, an axis 722, a cleaning liquid inlet 734, and liquid pumps or valves 731, 733, 735, 744 are provided. The mixing cup 710, the motor 720, the heating element 760, the optional sonicator 750, the sample inlet 730, the staining composition inlet 732, the outlet 742, the axis 722, the cleaning liquid inlet 734 form a mixing unit. A cross-sectional view of the mixing unit is presented in FIG. 8.

The mixing cup 710 is for mixing a liquid sample with a staining composition and forming a receptacle to hold a mixed liquid while the mixed liquid is sonicated and/or has to incubate. The mixing cup 710 is arranged rotatable around a virtual axis. The mixing cup 710 may be coupled to the motor 720 by means of an axis 722, but the motor may also provide a rotational force to the mixing cup 710 by other means, such as a magnetic arrangement. In such a magnetic arrangement the motor rotates a permanent magnet and the bottom of the mixing cup 710 also has a permanent magnet and the rotated permanent magnet applies a rotational force to the permanent magnet of the mixing cup 710. If the liquid sample is received from the liquid sample inlet 730 and the staining composition is received from the staining composition inlet 732, the mixing cup 710 may be slowly rotated to mix the liquid sample and the staining composition to obtain a mixed sample 712. The mixing cup 710 can also be rotated at a relatively high speed such that centrifugal forces move the liquid 712 in the mixing cup 710 out of the mixing cup 710.

The mixing cup 710 may have tilted walls such that the diameter of the mixing cup 710 increases at positions closer to the opening/top side of the mixing cup 710. In a practical embodiment, the 3d shape of the interior walls of the mixing cup 710 is the shape of a truncated cone. Furthermore, FIG. 7 shows that the walls of the mixing cup 710 are relatively thin. This may be an advantage because heat can be easily transferred through the walls from the outside of the cup towards the interior of the cup. Embodiments of the mixing cup 710 are not limited to embodiments with a thin wall. For reasons of mechanical and/or thermal stability, it might be that the walls of the mixing cup 710 are relatively thick or the interior of the mixing cup is formed in a solid disk resulting in walls that are thicker near the bottom of the mixing cup 710.

The mixing cup 710 may be manufactured of the material stainless steel. This results in a high thermal conductivity, high oxidation resistance and in combination with proper post-processing steps such as polishing in a smooth, and therefore easy cleanable surface Alternative materials that could also be used are materials with good thermal conductance properties known in the art.

The liquid sample inlet 730 is, for example, a tube through which the liquid sample is dispensed into the mixing cup 710. Other means inside the apparatus 700 may provide the liquid to the liquid sample inlet 730. For clarity, an optional pump or valve 731 is drawn which is able to control the flow of the liquid sample into the mixing cup 710. In practical embodiments, the apparatus 700 comprises an intake and sample module which obtain the liquid sample from, for example, a receptacle that contains the liquid for which a cell count must be obtained. Such an intake and sample module may also obtain the liquid sample from a continuous process.

The staining composition inlet 732 is, for example, a tube through which the staining composition is dispensed into the mixing cup 710. The staining composition comprising the dimeric nucleic acid dye and the buffering agent. The dimeric nucleic acid dye has the formula Q1-BRIDGE-Q2, wherein Q1 and Q2 are nucleic acid dye moieties and BRIDGE is connecting Q1 and Q2 Other means inside the apparatus 700 may provide or prepare the staining composition. For example, the staining composition may be obtained with a pump from a cartridge containing the staining composition. For example, the staining composition is prepared in a preparation module inside the apparatus 700 if the staining composition is not available as a mix but only the raw materials of the staining composition are available. Also for clarity, it has been drawn that the staining composition inlet 732 may comprise an optional pump or valve 733 for controlling the dispensing of the staining composition into the mixing cup 710.

An optional cleaning liquid inlet 734 is drawn which provides a cleaning liquid to the interior of the mixing cup 710 at moments in time that the mixing cup 710 must be cleaned. The cleaning liquid inlet 734 may comprise a pump or valve 735 that controls the dispensing of the cleaning liquid into the mixing cup 710. For example, after emptying the mixing cup 710, the cleaning liquid is provided at about the center of the bottom surface of the mixing cup 710 and the mixing cup 710 is rotated relatively fast such that the cleaning liquid moves along bottom surface and the wall(s) of the mixing cup 710 out of the mixing cup 710. The used cleaning liquid is, for example, water+Triton X-100, Decon 90, NaClO 0.1-1.0%, or Surfonic JL80x. Alternatives to Triton that may be used in the methods of the present invention are phosphoric acid tributyl ester, oxirane, 2-methyl polymer with oxirane, sorbitan, mono-(9Z)-9-octadecenoate, poly(oxy-1,2-ethanediyl, mono-dodecanoate, poly(oxy-1,2-ethanediyl) derivatives, alcohols, C9-11, D-gluco-pyranose, oligomeric decyl octyl glycosides, D-gluco-pyranose, oligomeric, C9-11 alkyl glycosides, poly (oxy-1,2-ethanediyl) alpha (2-propyl-heptyl)-ω-hydroxy, oxirane, 2-methyl-, polymer with oxirane, mono(2-ethylhexyl) ether. Close to the wall of the mixing cup 710 is provided a heating element 760 that also comprises a heater and a sensor. Heat heating element 760 is arranged at a position where it does not hinder the rotation of the mixing cup 710 and where heat generated in the heating element 760 is well transferred to the wall of the mixing cup 710. In practical embodiments there is a gap of about 1 mm between the heating element 760 and the mixing cup 710. The heating element 760 provides heat to the mixing cup if the heating element 760 receives a heater control signal indicating that heat must be generated. A sensor (not shown separately) may be provided in the heating element 760 at a position as close as possible to the mixing cup 710 and measures the temperature of the heating elements and/or the mixing cup 710. The sensor may also be provided at another location close to the mixing cup 710 to measure the temperature of the mixture in the mixing cup 710. The measured temperature is used to control the heater to obtain a specific temperature of the liquid 712 inside the missing cup 710. The heater and the sensor are optionally coupled to the controller 770 to form a control loop. The controlling of the heater and the use of a sensor arranged close to the mixing cup 710 enables also that the temperature change of the liquid 712 over time can be well controlled. In FIG. 7 the heating element 760 is only drawn at one side of the mixing cup 710, however, the heating element may have several elements that are arranged at several relative positions with respect to the mixing cup, or the heating element may enclose the whole mixing cup 710 such that the temperature of the liquid 712 in the mixing cup 710 can be better controlled and the liquid 712 can be heated faster. In the presented embodiment of the apparatus 700, the heating element 760 is not directly in contact with the mixing cup 710 and a gap is present between the heating element 760 and the mixing cup 710. Embodiments of the apparatus 700 are not limited to the presented embodiments. In alternative embodiments, the heating element 760 is integrated in the mixing cup such that the heat is generated as close as possible to the liquid 712 and such that the sensor can more accurately measure the temperature of the liquid 712 inside the mixing cup 710. If the heating element 760 is integrated in the mixing cup 710, means have to be provided to transfer power to the heating element 760 and communicate the control signals and measurement signals from the controller 770 to the heating element 760 and vice versa.

The liquid sample and the staining composition have been mixed into a mixture in the mixing cup 710, the sonicator 750 at least extends for a predefined distance into the liquid 712 in the mixing cup 710. Optionally, at well-defined moment in time, when the mixture is in the mixing cup 710, the sonicator provides energy to the mix by means of ultrasound. The sonicator 750 operates, for example, at 20 to 40 kilo Hz and provides, for example, 1 to 5 watt to the mix during a period of, for example, for 5 to 10 seconds. In one embodiment the sonicator 750 is moveable by means of an actuator and moves partially into the liquid 712 in the mixing cup 710 at the moment in time that it has to provide the energy in the form of ultrasound to the liquid 712. Another term for "sonicator" is "ultrasonic probe".

The outlet 742 is, for example, a tube that is inserted into the liquid 712 that is present in the mixing cup 710 at the moment in time that the liquid 712 is ready for being analyzed. The outlet 742 may have a permanent position such that it is always in the liquid 712 when the liquid sample and the staining composition are mixed in the mixing cup 710, or the outlet 742 may be movable by means of an actuator such that the tip of the outlet 742 is in the liquid 712 when a portion of the liquid 712 must be pumped up. The outlet 742 may have a pump 744 for pumping up a sample of the liquid 712 and for proving the sample to the measurement module 740. When the outlet 742 has taken a sample from the liquid 712 and provided to the measurement module 740, the mixing cup 710 may be emptied by the previously described relatively fast rotation of the mixing cup 710.

Optionally, all inlets 730, 732 and the outlet 742 may also be coupled to a system that cleans the interior of the inlets 730, 732 and the outlet 742 once the samples or staining composition passed the respective inlets 730, 732 and the outlet 742.

The outlet 742 is coupled to the measurement module 740. The measurement module 740 is configured to count stained cells in the sample that is provided by the outlet to the measurement module 740. In an embodiment, the measurement module 740 is a flow cytometer, a fluorescence microscope, a fluorometer or a fluorescence plate reader.

The apparatus 700 optionally has a controller 770 for controlling the different components of the apparatus 700. For example, the controller 770 is coupled to the motor 720, to the heating element 760, to the optional sonicator 750, to the pumps/valves 731, 733, 735, 744 and to the measurement module 740. The controller 770 may also be coupled to other components of the apparatus 700 that are not drawn. The coupling between the controller 770 and the components of the apparatus 700 may be implemented by means of, for example, a CAN (controller area network) bus. Via the CAN bus signals and/or messages can be communicated from the controller 770 to the components and vice versa. For example, the heating element 760 receives via connection 772 a signal indicating whether the heater has to generate heat or not and via connection 772 the measurements of the temperature sensor may be provided to the controller 770. The connections between the controller 770 and the above discussed controllable elements of the apparatus 700 can be formed by wired connections, may also be formed by wireless connections or may also be formed by optical communication signal that are guided through optical fibers.

The measurement module 740 may also be controlled by the controller 770 at least in so far it concerns starting and stopping the measurement. In a practical embodiment, the measurement module 740 is also coupled to a data processing unit which receives the measured data and processes this data for further use, such as, for example, presenting the measurement results on a display.

The process of counting cells, such as bacteria, in a liquid sample is a well-defined series of steps and the timing of the steps may be well-defined as well. In certain steps the timing may be critical. The controller 770 is the unit which is aware of the well-defined series of steps and the required timing. The controller 770 controls the several components accordingly.

Specifically in the context of this document, the controller 770 is configured to: a) controlling the sample inlet 730 and the staining composition inlet 732 to dispense the liquid sample and the staining composition into the mixing cup; b) controlling the mixing cup to mix the liquid sample and the staining composition in the mixing cup to obtain the mixture—the controlling of the mixing cup may be executed by controlling the motor 720; c) optionally controlling the optional sonicator 750 to sonicate the mixture; d) controlling the heating element 760 to heat the mixture to a temperature to incubate the mixture, during the incubation the temperature and/or the pH of the mixture renders the nucleid acid dye cell-permeant; e) optionally controlling the optional sonicator 750 to sonicate the incubated mixture; f) controlling the outlet 742 to provide the mixture or a pat part thereof to the measurement module 740; and g) controlling the measurement module 740 to count cells that are stained with said dye within the mixture or the part thereof. Controlling the sample inlet 730, controlling the staining composition inlet 732 and controlling the outlet 742 may involve controlling the valves or pumps 731, 733, 744.

The controller 770 may also be configured to control the motor 720 to rotate the mixing cup 710 at high speed and control the cleaning liquid inlet 734 to dispense a cleaning liquid into the mixing cup 710 while the mixing cup 710 still rotates at the relatively high speed. When the mixing cup 710 is cleaned, the controller 770 may control the start of a subsequent mixing, sonicating, incubating and measurement procedure. This paragraph describes that the apparatus 700 performs the steps sequentially, but it has to be noted that several steps may also be performed in parallel by the apparatus 700. For example, if a sample is provided to the measurement module 740 and while the measurement module 740 is still counting the stained cells in the sample, as soon as possible another mixing step may be started. Embodiments of the apparatus 700 are not limited to apparatuses 700 with only one mixing cup 710 and/or one measurement module 740. The apparatus 700 may also have several instances of all the above discussed elements of the apparatus for performing several activities in parallel such that the apparatus can analyze more liquid samples per hour.

Basically, the task of the controller 770 is to operate the apparatus 700 in such a way that the apparatus 700 executes an embodiment of the previously discussed methods. Thus, the controller 770 is configure to control the apparatus 700 to execute an embodiment of the previously discussed methods. In practical embodiments, the controller 770 comprises a computer program comprises instructions to allow the controller 770 to control the apparatus 700 to execute an embodiment of the previously discussed methods. The controller 770 may also be based on dedicated hardware that is configured to control the apparatus 700 to execute an embodiment of the previously discussed methods.

FIG. 8A schematically shows a three dimensional view of a mixing unit 800 of the apparatus for counting cells, such as bacteria, in a liquid sample. The mixing unit 800 is similar to the mixing unit 700 of FIG. 7. Embodiments of the shown elements and the function of the shown elements have been discussed in the context of FIG. 7. The three dimensional view of FIG. 8A shows the elements: the mixing cup 810, the sonicator 850, the sample inlet 830, the staining composition inlet 832 and the outlet 842.

FIG. 8B schematically shows a cross-sectional view of the mixing unit 800 of FIG. 8A. FIG. 8B schematically shows the elements: the mixing cup 810, the sonicator 850, the axis 822, and the sample inlet 830. The mixing cup 810 is enclosed by a thermal mass 862 in which a heating element similar to heating element 860 is embedded. The thermal mass 862 is heated and, because the distance between the thermal mass 862 and the mixing cup 810 is relatively small, the mixing cup 810 is heated as well. In the thermal mass 862, close to the mixing cup 810, the temperature sensor that senses the temperature of the mixing cup 810 is provided. The thermal mass 862 is made of, for example, a metal such as, for example, stainless steel.

Figure 9:
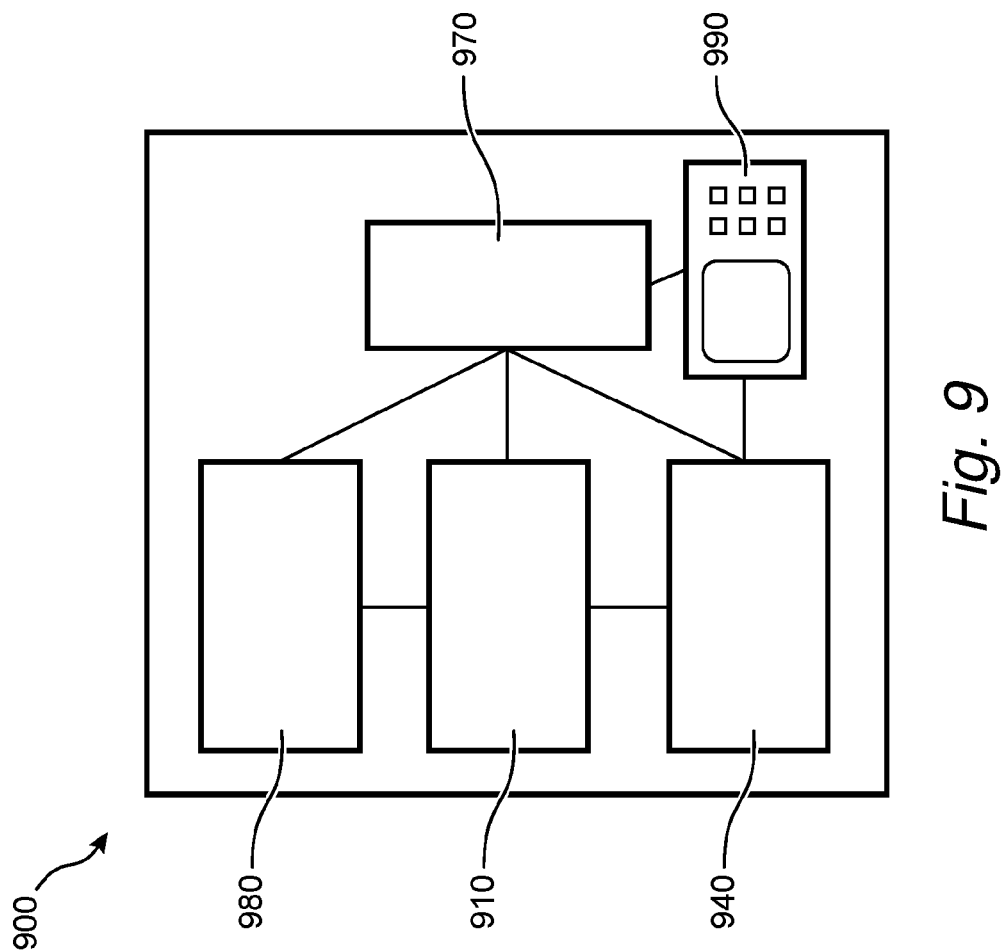
FIG. 9 schematically shows a further apparatus for counting cells in a liquid sample.

FIG. 9 schematically shows further apparatus 900 for counting cells in a liquid sample. The further apparatus 900 for cells in a liquid sample comprises an intake and sample unit 980, a mixing unit 910, a measurement unit 940, a controller 970 and an user interface unit 990. Embodiments and the function of the mixing unit 910, the measurement unit 940, and the controller 970 have been discussed previously in the context of FIG. 7, FIG. 8A and FIG. 8B, wherein only the first digit of the three-digit reference numbers are different depending on the figure.

The sample and intake unit 980 is a unit that samples the liquid in which the cells must be counted and provides the sample to the mixing unit 910. The sample and intake unit 980 also takes in other liquids and/or other materials that must be provided to the mixing unit 910. Examples are, for example, the previously discussed staining composition and the previously discussed cleaning liquid. In an embodiment, the raw materials of the staining composition are taken in by the sample and intake unit 980 and provided to the mixing unit 910 and/or mixed before being provided to the mixing unit 910. In an embodiment, the sample and intake unit 980 takes in water and cleaning materials that are mixed with or dissolved in the water to obtain the previously discussed cleaning liquid. The sample and intake unit 980 may comprises a compartment in which bottles with the liquid-to-be-sampled and other liquids are placed. For example, automated pipettes suck up liquids from the bottles. In another example, the sample and intake unit 980 comprises couplings for coupling the sample and intake unit 980 by means of pipes or tubes to external containers that comprise the liquids to be sampled and to be taken in.

As discussed previously, the liquid sample of which cells have to be counted and the staining composition are mixed, sonicated and incubated in the mixing unit 910. As discussed previously, the mixing unit 910 is coupled to the measurement unit 940 and a mixed, sonicated and incubated sample is provided to the measurement unit 940. The measurement unit 940 counts the cells in the received sample. Examples of the measurement unit are: a flow cytometer, a fluorescence microscope, a fluorometer or a fluorescence plate reader.

The measurement unit 940 is coupled to a user interface unit 990. The measurement unit 940 provides the measured results to the user interface unit 990. The user interface unit 990 may comprise a data storage in which the measured results are stored. The user interface unit 990 may also comprise a processing unit for processing the measured results and for preparing the results in an appropriate format for presentation to a user. The user interface unit 990 may comprise, for example, a display for presenting the measured and processed results to the user. The user interface unit 990 may also comprise a keyboard for receiving user commands from the user. The user may, for example, adapt the information presented on the display by providing specific user commands. In another embodiment, the display is a touch sensitive display that is also suitable for receiving user commands.

The further apparatus 900 comprises a controller 970 for controlling the operation of the further apparatus 900. The controller 970 is coupled to the previously discussed units and provides operational commands to these units and may receive information from the units. Such received information is, for example, sensor information, information relating to the progress of the activities performed by the different units and/or error messages generated in the different units. As discussed previously, the controller 970 also controls the timing of the activities performed by and/or tasks of the different units. The controller 970 is also coupled to the user interface unit 990 such that the user interface unit 990 is able to present information about the progress of the analysis of the liquid-to-be-sampled. The user interface unit 990 may also be used to receive user commands that, for example, start the operation of the further apparatus 900 and/or that interrupt the operation of the further apparatus in an emergency situation.

It should be noted that the above-mentioned embodiments illustrate rather than limit the invention, and that those skilled in the art will be able to design many alternative embodiments.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Validation of GelGreen™ Staining of Bacteria

Figure 2:
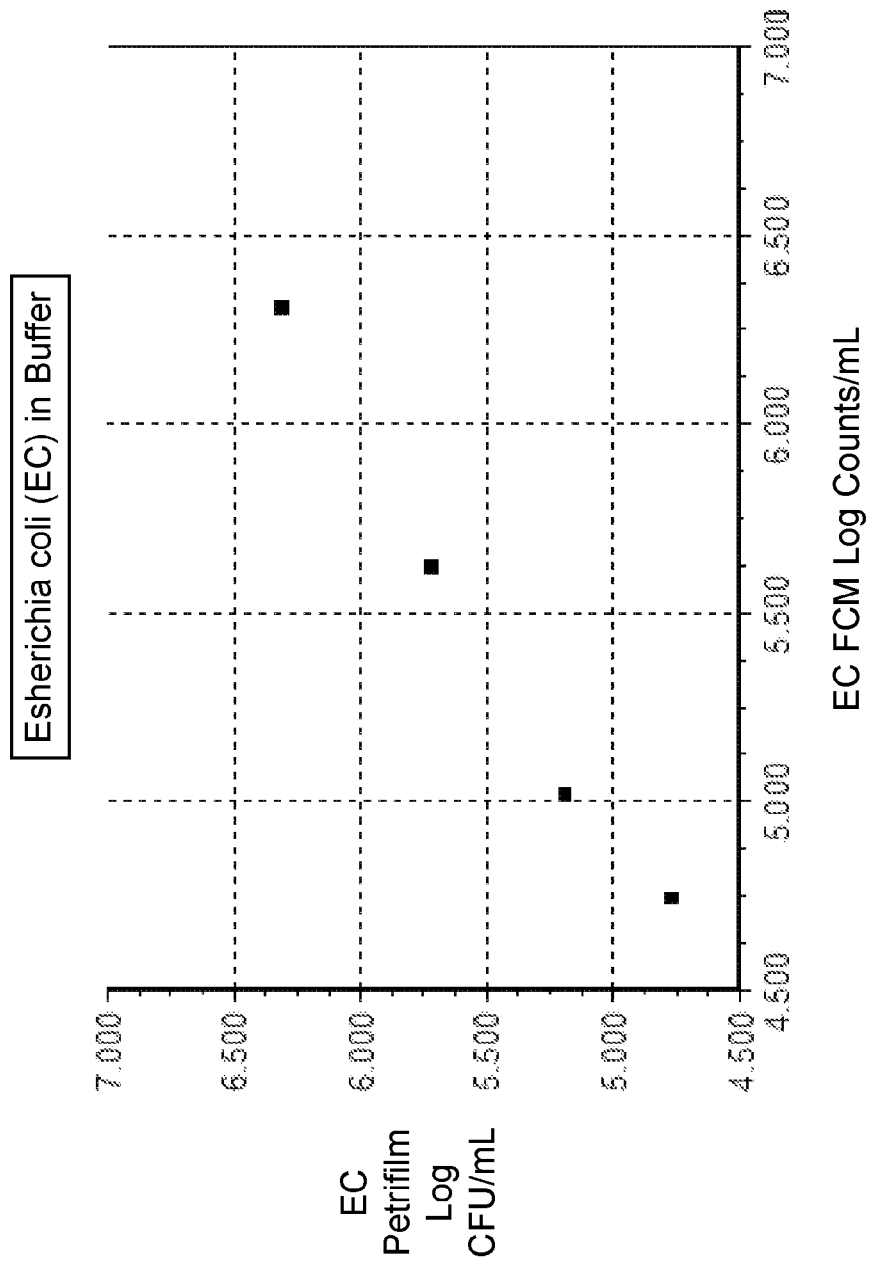
FIG. 2 shows a clear linear relationship in a plot between the log of the flow cytometer bacterial counts using Gel-Green™ versus the log CFU counts from a Petrifilm™ count.

First, an experiment was performed to confirm that bacterial counts obtained on the flow cytometer using GelGreen™ did correlate with traditional plate counts. For this, the Petrifilm method was selected (Standard Methods for Examination of Dairy Products $17^{th}$ Edition 2004. Edited by H. M. Wehr and J. R. Frank. American Public Health Association, 800 I Street, NW, Washington D.C. 200001. Chapter 6.040), rather than a poured agar plate method, because of ease of use. *Escherichia coil* (*E. coli*) cultures were grown at 36° C. in Trypticase Soy Broth (TSB) in a culture tube. A staining composition was prepared as follows: The nucleic acid dye GelGreen™ (from Biotium) was diluted to 1× from the 10,000× commercially available stock, into Tris-buffered saline (100 mM Trizma base, 100 mM Trizma HCl, 150 mM NaCl, pH 8.5), which was preheated to 50° C. The used dilution of 1:10,000 of the GelGreen™ is in accordance with the manufacturer's recommendation for using GelGreen™ for the purpose it was intended for, namely staining DNA in an agarose gel. This is the dilution of GelGreen™ used in all the examples herein. The *E. coli* culture was removed from the 36° C. incubator and a small volume was diluted 1:100 into the preheated staining composition and incubated for approximately 4.5 min at 50° C. The stained *E. coli* was analyzed on the flow cytometer and the FL1 (Bandpass 531 nm (519-551)) and FL2 (Long pass >550 nm) fluorescence channels were used to identify the stained bacteria (FIGS. 1A and 1C). A rectangular region was defined around the positively stained cells identified as live cells in the FL1 versus FL2 2-dimensional correlation plot (FIG. 1B). A count per mL of the *E. coli* was obtained from the flow cytometry analysis. The *E. coli* culture was then diluted in TSB to obtain 3 different concentrations (1:10, 1:100 and 1:1000, respectively). The *E. coli* cultures were kept at 4° C. to minimize further growth until analysis. Each dilution of *E. coli* was stained with the GelGreen™ reagent, analyzed on the flow cytometer and counts for each dilution were obtained. Each *E. coli* culture was also appropriately diluted in Butterfield's PBS and 1 mL of the appropriately diluted culture was plated on Petrifilms in duplicate. The Petrifilms were placed in a 30° C. incubator, removed after 48 hrs and the colonies on each Petrifilm were counted using an automated colony counter. An average CFU/mL for each *E. coli* dilution was obtained. The Log of the flow cytometer bacterial counts using GelGreen™ was plotted versus the Log CFU counts from the Petrifilm (FIG. 2). A clear linear relationship between the two methods is shown, which shows that the dye enters bacteria cell membranes under the conditions mentioned, and also stains the DNA/RNA of these bacteria.

Example 2

Staining of E. coli in Raw Milk Treated with GelGreen™

To show where the bacteria in the FL1 and FL2 signal plots can be expected, bacteria were first counted in the staining composition without adding any milk. A culture of E. coli were grown at 36° C. in Trypticase Soy Broth (TSB) in a culture tube. The nucleic acid dye GelGreen™ was diluted into Tris-buffered saline, at approximately pH 8.5, which was preheated to 50° C. The E. coli culture was removed from the 36° C. incubator and a small volume was diluted 1:100 into the preheated staining composition and incubated for approximately 4.5 min at 50° C. The stained E. coli was analyzed on the flow cytometer and the FL1 and FL2 fluorescence channels were used to identify the stained bacteria (FIG. 3A).

To show how the FL1, FL2 signals look like in un-spiked raw milk, low bacterial count raw milk was analyzed. The locally obtained raw milk (generally from a farm) has a very low bacteria count ranging from 1000 to 50,000 CFU per mL. The staining composition comprising GelGreen™ as the nucleic acid dye was prepared in the same way as in Example 1, except that the protease Savinase® 16L (from Novozymes) was added in an amount of $1.92 \times 10^3$ NPU/ml, where NPU is "Novo Protease Unit which is the same as Anson unit (AU). The staining composition was preheated to approximately 50° C.; a small volume of raw milk sample was preheated just long enough for the sample to reach approximately 50° C.; the preheated sample was diluted about 1:10 in the preheated staining composition; the sample with the staining composition was sonicated for approximately 5 seconds at 22.5 kHz. This was preferably done by direct placement of the sonicator probe into the sample, but may also be performed indirectly by placing the appropriate sonicator probe against the sample tube. The sample with the staining composition was incubated at approximately 50° C. for approximately 4 to 5 min; the sample was again sonicated for approximately 5 seconds and finally the sample was analyzed on the flow cytometer and the fluorescent signals from the bacteria were detected and a count per unit volume was determined. Further research was performed that showed that even better staining was achieved at slightly higher temperatures (56° C. and more preferably at 62° C.).

Figure 3:
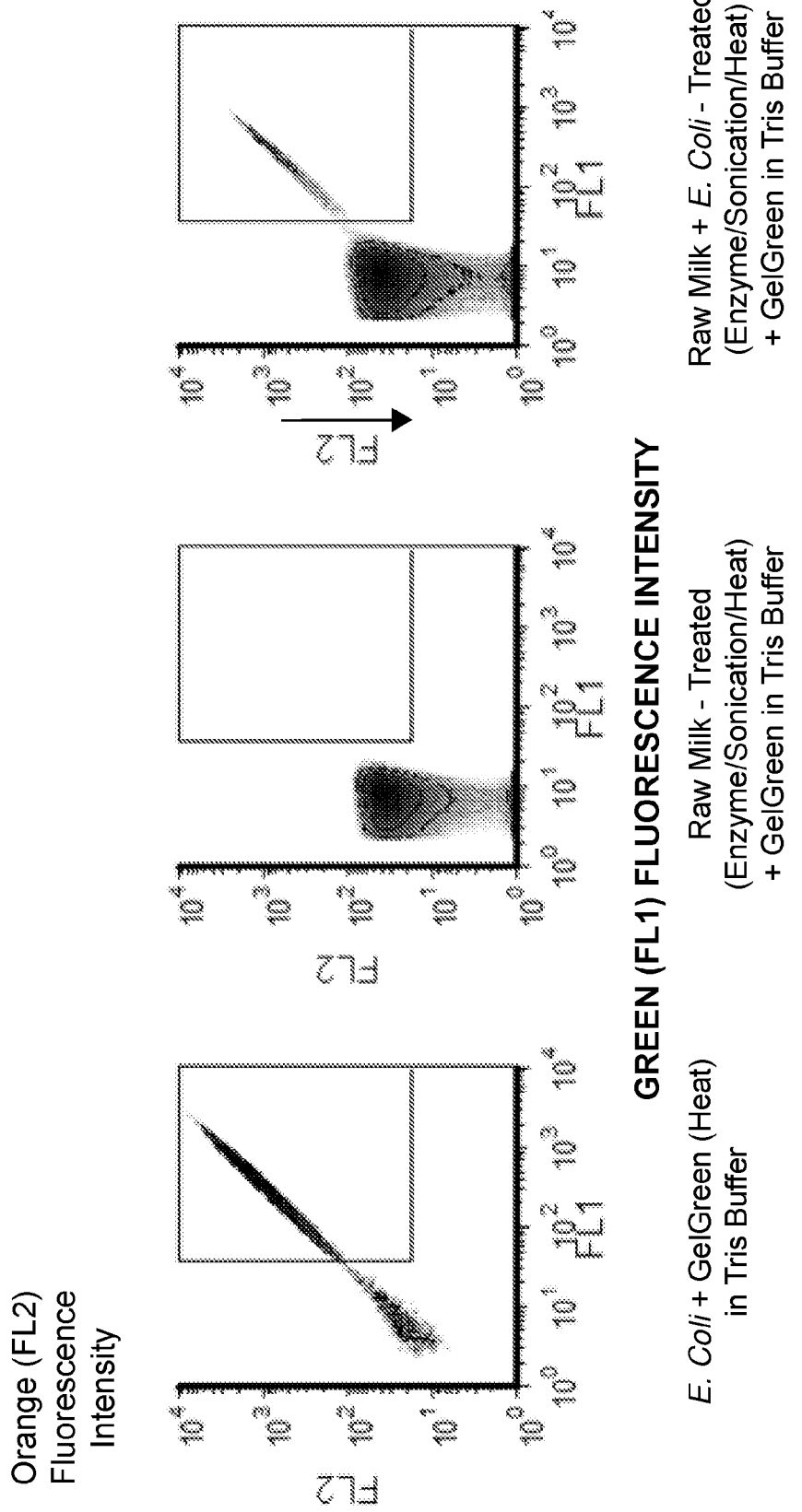
FIG. 3 shows flow cytometry data of *E. coli* stained with GelGreen™ in (A) Tris-buffered saline (pH 8.5), (B) raw milk to which no bacteria were added but which was treated according to the protocol of the present invention, and (C) a raw milk sample to which *E. coli* bacteria were spiked. A clear population of *E. coli* was identified in the spiked raw milk, overlapping with the FL1FL2 count region.

A small volume of raw milk was processed and analyzed following this GelGreen™ raw milk treatment staining method protocol (FIG. 3B). To show the FL1 and FL2 signals for spiked raw milk, a known number of E. coli were placed into a known volume of the same raw milk and kept at 4° C. until treated, stained and analyzed on the flow cytometer. The raw milk with E. coli was processed and analyzed using the same GelGreen™ raw milk treatment staining method protocol. A clear population of E. coli was identified in the raw milk, falling within the FL1FL2 count region (FIG. 3C). The FL1FL2 count region is shown by the square gating in FIGS. 3A,B and C and is also identified based on the results of FIGS. 3A, B and C. This clearly shows that the method as disclosed herein, provides for a fast way of tracing bacteria can be traced in raw milk samples.

Example 3

Validation of Bacterial Flow Cytometry Counts in Raw Milk

Figure 4:
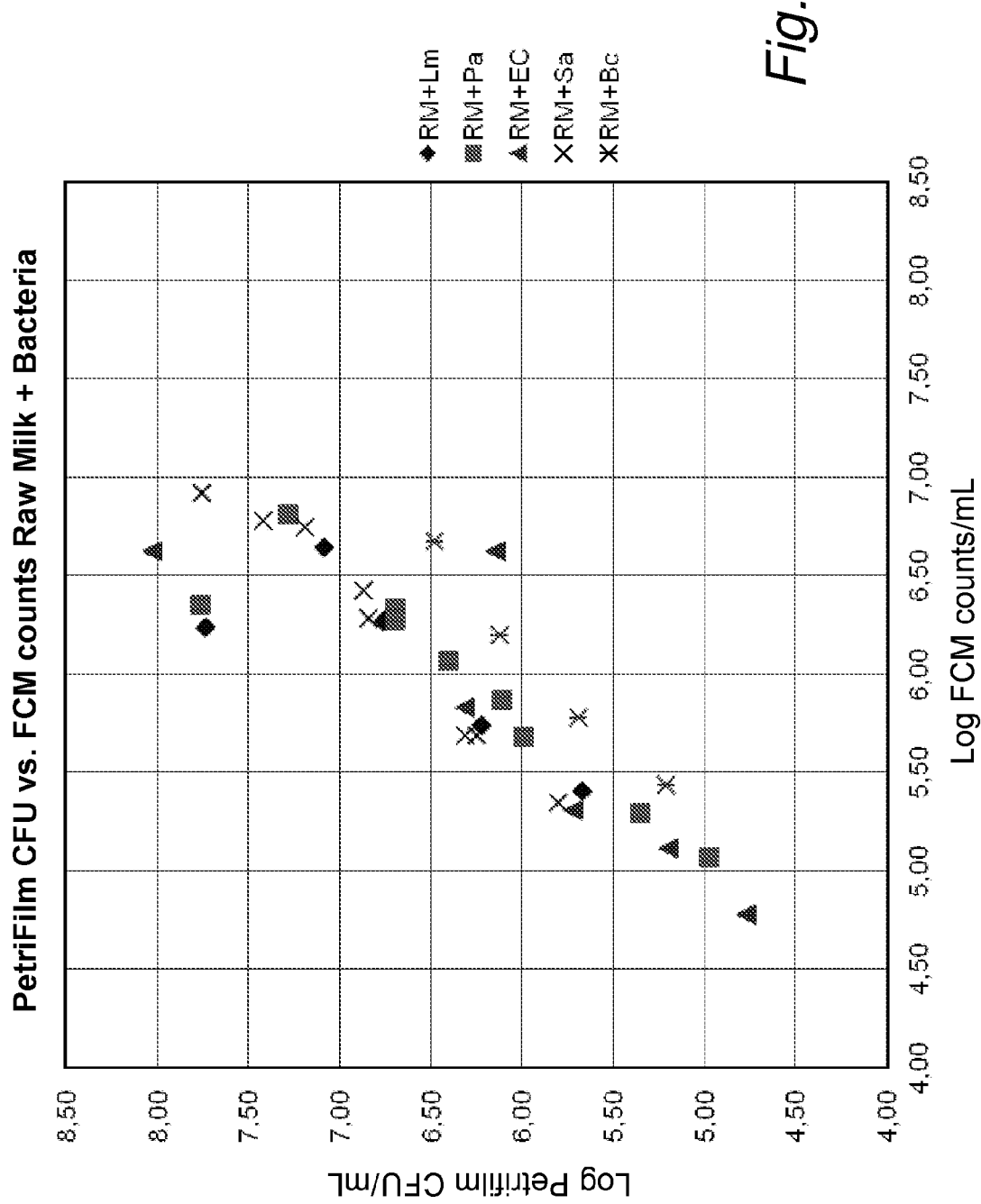
FIG. 4 shows a plot of log flow cytometer (FCM) counts per mL versus the log Petrifilm™ CFU per mL counts of raw milk (RM) samples spiked with different types of bacteria. Abbreviations of the bacteria is as disclosed in example 3.

A selection of gram negative and gram positive bacteria were chosen to be placed into raw milk and processed and analyzed following the GelGreen™ raw milk treatment staining protocol as disclosed in example 2. Results are shown in FIG. 4. The gram positive organisms selected were Listeria monocytogenes (Lm), Staphylococcus aureus (Sa), and Bacillus cereus (Bc). The gram negative organisms selected were Pseudomonas aeruginosa (Pa) and Escherichia coil (Ec). Different concentrations of each culture were placed into a sample of raw milk and kept at 4° C. until processed. Each sample of raw milk with an individual bacterial culture was processed and analyzed following the GelGreen™ protocol as described in example 2. Each sample of raw milk with an individual bacterial culture was appropriately diluted in Butterfield's PBS and 1 mL was plated on Petrifilms in duplicate and CFU/mL were obtained. The resulting Log FCM counts per mL were plotted against the Log Petrifilm CFU per mL. This shows an overall linear relationship (with some outliers) providing validation of this novel method.

Example 4

Staining E. coli with different Nucleic Acid Dyes

A culture of E. coli was grown at 36° C. in Trypticase Soy Broth (TSB), stained with GelGreen™ and counted on the flow cytometer (FIG. 5) as described in example 2. The E. coli culture was then kept at 4° C. until stained with other nucleic acid dyes. The nucleic acid dyes TOTO®-1 and SYBR® Safe (both from Thermo Fisher Scientific) were selected as alternatives. TOTO®-1 is a dimer of the unsymmetric cyanine dye Thiazole Orange, and is cell impermeant. SYBR® Safe is a DNA gel stain that has been specifically developed for reduced mutagenicity, however unlike GelGreen™ it readily crosses the membrane of cells. Both dyes have similar spectral properties to GelGreen™ and were diluted in Tris-buffered saline using the same dilution factor as GelGreen™. Staining of E. coli was either performed at room temperature (~23° C.) or at 50° C. for approximately 4.5 min, analyzed on the flow cytometer and counts were obtained using the FL1FL2 count region. GelGreen™ was furthermore diluted in a 150 mM NaCl solution and used to stain E. coli at 23° C. and 50° C., analyzed on the flow cytometer and counts from the fluorescently labeled bacteria were obtained (four bars, left). The bacterial count data obtained using the flow cytometer from the different nucleic acid dyes at the two temperatures and in Tris-buffered saline pH=8.5 and saline solution, respectively, are shown in FIG. 5. This bar graph clearly shows that TOTO®-1 does not stain E. coli even when at 50° C. in Tris-buffered saline. It also shows that SYBR® Safe is cell permeant and does not need heating to stain E. coli. GelGreen™ does not stain E. coli at room temperature neither in NaCl solution nor in Tris-buffered saline. This is expected because GelGreen™ was specifically designed to not cross the membrane of cells. Very surprisingly however, GelGreen™ exhibits minimal staining of E. coli at 50° C. when in NaCl solution, but stains essentially all bacterial cells at 50° C. when in Tris-buffered saline.

Example 5

Figure 6:
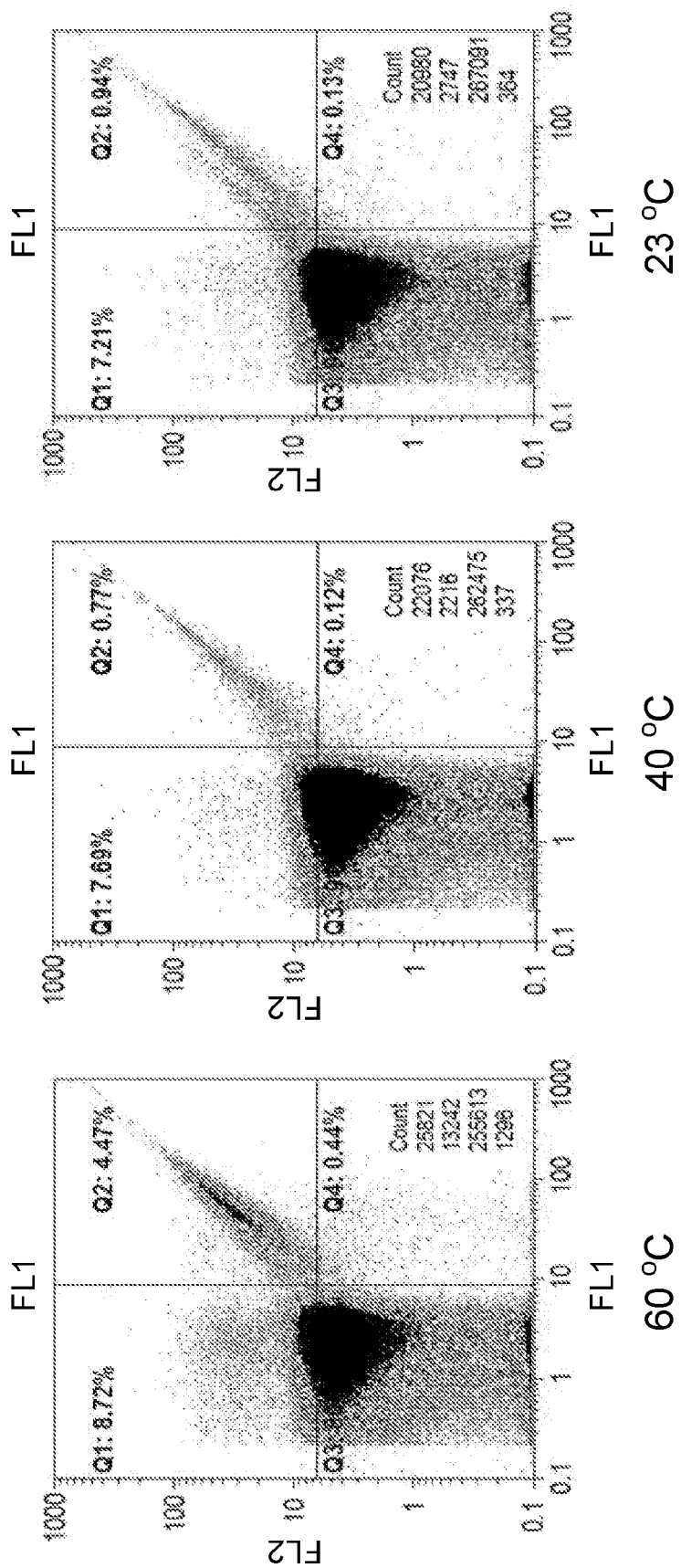
FIG. 6 shows flow cytometry dotplots of raw milk samples, spiked with *E. coli* and incubated with the protocol of the present invention (upper three panels), at respectively 60° C. (left), 40° C. (middle) and 23° C. (right). The lower three panels show the flow cytometry dotplots obtained by spiking, and incubating, water with 0.9% salt (saline) with *E. coli* using respectively 60° C. (left), 35° C. (middle) and 25° C. (right).
Figure 6:
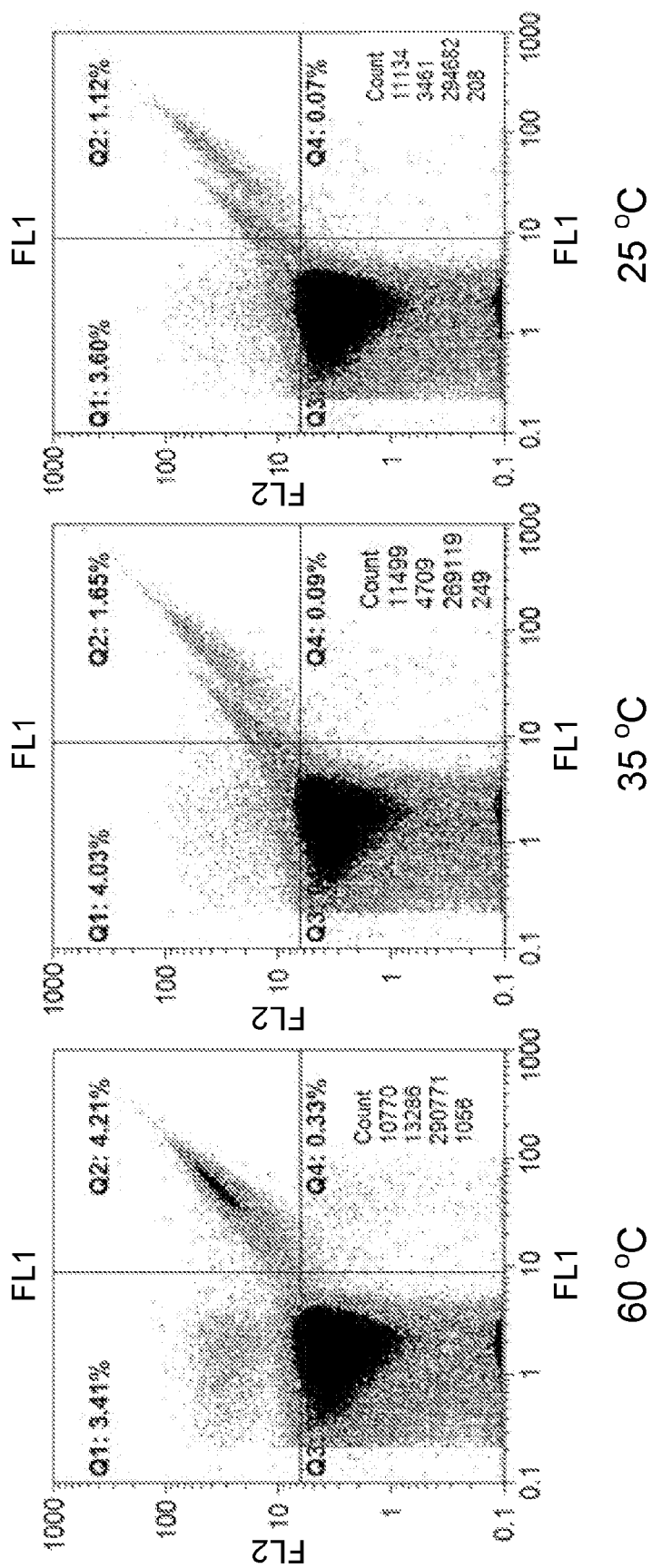

Staining *E. coli* with GelGreen™ in Raw Milk and Saline Using Different Temperatures To show that the method of the present invention is also applicable in other liquid samples than raw milk, two different spiked solutions were prepared: One based on raw milk and the other being water+0.9% salt (=150 mM NaCl also referred to as saline). Both solutions were spiked with *E. coli* bacteria by adding 200 μl bacterial culture to 45 ml solution. The staining composition was prepared with the same dilution of GelGreen™ (from Biotium) as described in Example 1, but this time into a Tris-saline solution (200 mM Trizma base, 150 mM NaCl, pH 10.6) further comprising 0.12 AU/ml liquid Alcalase® 2.4 L FG (from Novozymes). Incubations were as described in the previous examples, except that spiked raw milk samples were incubated at 60, 40 and 23° C. and spiked saline samples were incubated at 60, 35 and 25° C. for 1 minute. The results provided in FIG. 6 clearly show that when temperatures around 60° C. were used, more bacterial cells could be counted than when lower temperatures were used. Each panel contains four quarters: Q1, Q2, Q3 and Q4. The counts provided in Q4 represent the number of cells given in each of these four quarters. It is clear that in the left panels (in both upper and lower row), counts in Q2 are significantly higher and plots are more intense than in the middle and right panels. Other data (not shown) indicated that when this temperature around 60° C. was further fine-tuned, the optimal temperature for this dye and this pH appeared to be approximately 62° C. This quite specific temperature does not limit the scope of the invention because any temperature in which an originally cell-impermeable nucleic acid dye becomes cell-permeable would be appropriate. The optimal range as disclosed herein is 40 to 70° C., a further preferred range is 60 to 68° C. and a highly preferred temperature point is 62° C.

Example 6

Differentiation Between Somatic and Bacterial Cells in a Liquid Sample

Figure 10:
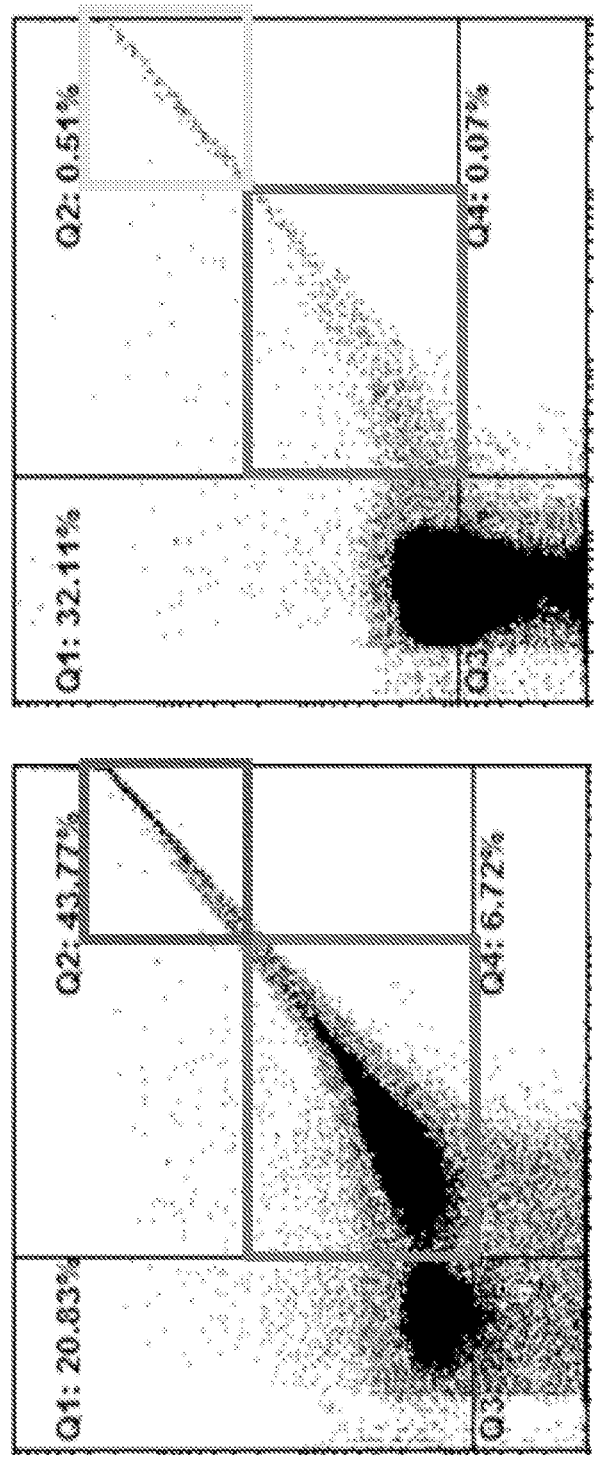
FIG. 10 shows flow cytometry dotplots of two different raw milk samples measured conform the protocol of the present invention. The left panel shows the dotplot from a high somatic cell count—and a high bacterial count sample, while the right dotplot is from a low somatic cell count—and low bacterial count sample. The rectangular FL1, FL2 regions in the pictures show the regions were bacteria are visible (lower left region) and the region were the somatic cells are visible (upper right panel).

It was also investigated whether in a single liquid sample a distinction could be made between somatic cells and bacterial cells. For this, 29 bulk tank milk samples were collected at different farms in the northern part of the Netherlands. All these samples were treated with the same staining composition as in Example 5. 200 μl of unheated raw milk was diluted with 1800 μl staining composition and incubated at approximately 62° C. for 1 minute; the sample is sonicated for 5 seconds at 40 kHz in the beginning and end of incubation and analyzed on the flow cytometer. The (gain) settings were fine-tuned to give optimal results for counting somatic cells and bacteria simultaneously. A rectangular somatic cell count gating was defined based on the pattern of the FL1 and FL2 fluorescence signals. The gating is shown by the upper right rectangular gating in FIG. 10. In this figure a high bacterial count—and high somatic cell count milk sample is shown on the left. On the right a low bacterial—and low somatic cell count milk sample is shown. The lower left rectangular gating defines the bacterial count area while the upper right gating defines the somatic cell count area.

Figure 11:
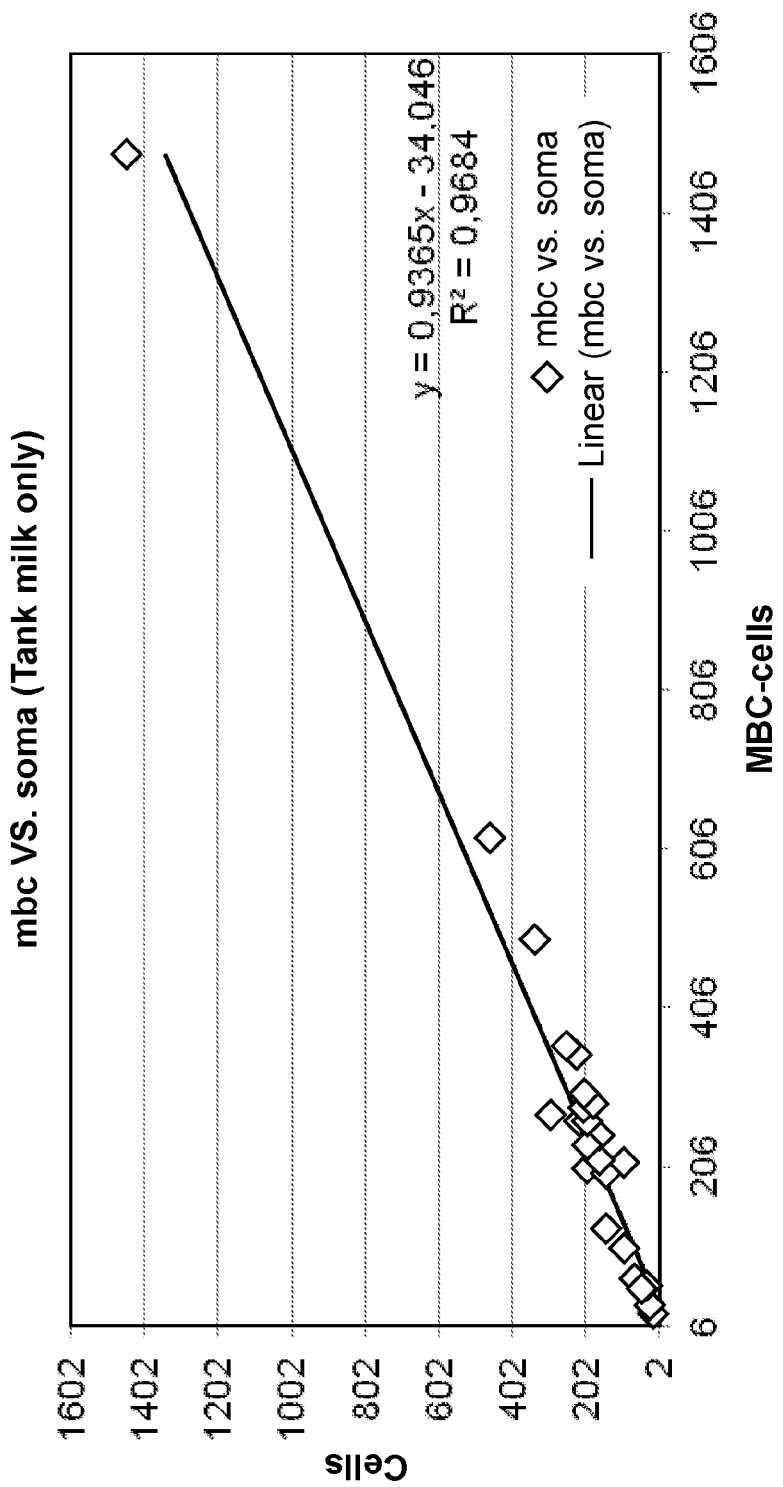
FIG. 11 is a correlation plot between somatic cell counts in 29 milk samples determined by a method according to the invention (y-axis) and a counts used by an established reference method (x-axis). The $R^2$ of this correlation was 0.9684.

The somatic cell count of all the 29 samples was determined by counting the dots in the upper right somatic cell count area. As a reference, the same bulk tank milk samples were analyzed by a SomaScope SMART (Delta Instruments, the Netherlands), which complies with ISO13366-2, to obtain a reference somatic cell count (MBC). Both results were plotted in a correlation plot in FIG. 11. The $R^2$ of this correlation is 0.9684.

Figure 12:
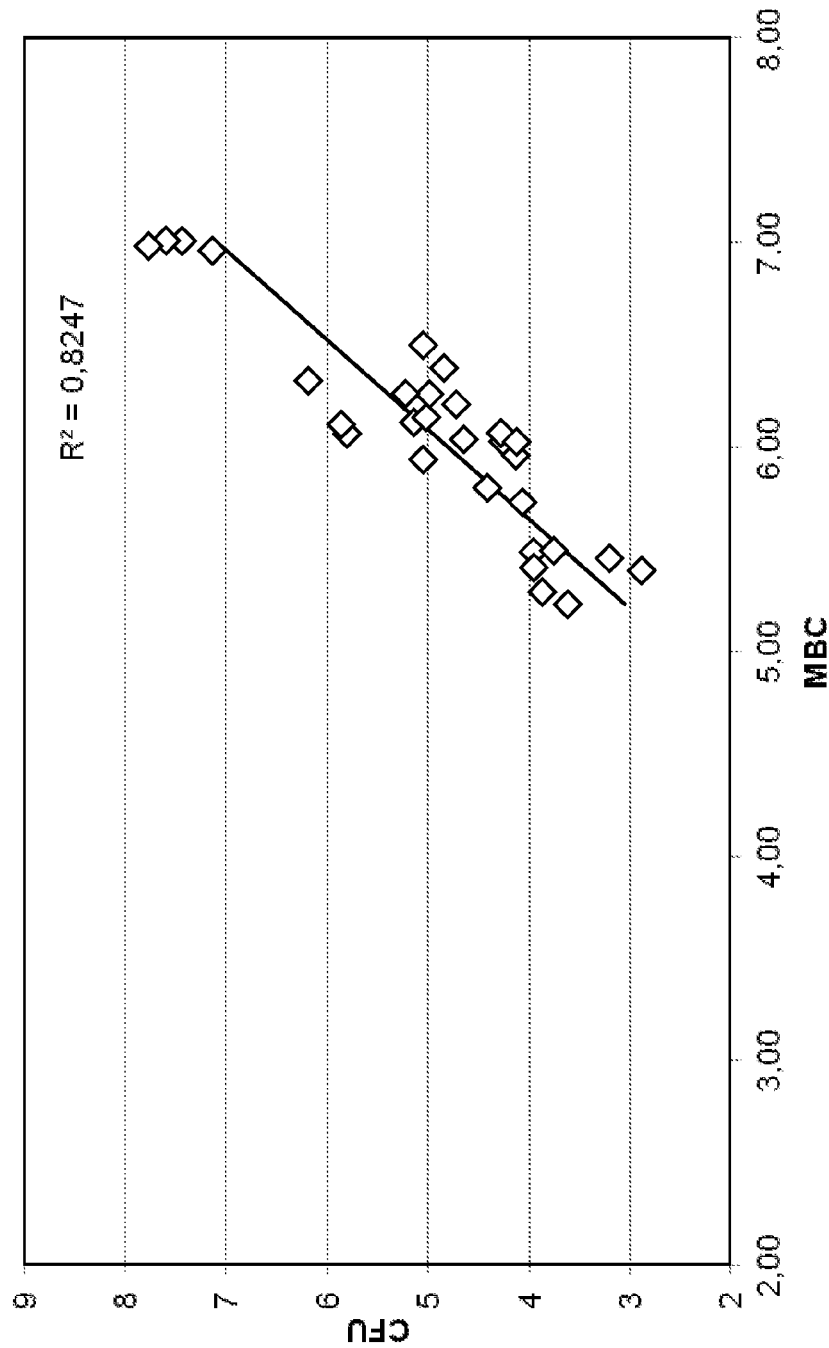
FIG. 12 is a correlation plot between bacterial cell counts in the same 29 samples by a method according to the present invention and the traditional plate count method used in the art. The $R^2$ of this correlation was 0.8247.

For every bulk tank milk sample the bacterial count was determined as well by counting the dots in the lower left rectangular gating. Traditional Petrifilm Aerobic Count Plates (AOAC Official Method 986.33) were used to obtain a bacterial reference count for all the 29 bulk tank milk samples. In FIG. 12 the correlation results of the bacterial counts is shown. The $R^2$ of this correlation is 0.8247.

These ($R^2$) results clearly show the ability to count somatic cells and also bacteria in the same time by using the same fluorescence signals FL1 and FL2.

To verify this method with Savinase®, locally obtained raw bulk tank milk from a dairy plant was collected. The 24 h old raw milk does not have a high bacterial count therefore an *E. coli* is grown overnight (approx. 15 h) in TSB at 32° C. An amount of 200 μl bacterial culture is added to a 45 ml volume of 24 h old raw bulk milk and kept at 4° C. until analyzed.

The staining composition comprising GelGreen™ as the nucleic acid dye was prepared in the same way as in Example 5, except that the Alcalase® protease was replaced by 0.12 KNPU/ml Savinase® 16L protease (from Novozymes). 200 μl of unheated raw milk is diluted with the 1800 μl staining composition and incubated at approximately 68° C. for 1 minute; the sample is sonicated for 5 seconds at 40 kHz in the before and after the incubation step and analyzed on the flow cytometer; the fluorescent signals from the bacteria were detected and a count per unit volume was determined.

Traditional plate counts were used to obtain a bacterial reference count. As used herein, the term "traditional plate counts", refers to Petrifilm Aerobic Count Plates (AOAC Official Method 986.33). The LOG of individual bacterial count (IBC)/ml from 24 h raw milk in the flow cytometer is 5.61, the LOG of CFU/ml petrifilm is 4.83. The LOG of IBC from 24 h raw milk spiked with *E. coli* LOG in the flow cytometer is 6.48. The LOG of CFU/ml petrifilm is 6.69. This experiment showed the same good correlation between IBC/ml and CFU/ml as shown in FIG. 12 (data not shown).

Example 7

Exploring Different Cell-Impermeant Dyes

The nucleic acid dyes, Evagreen®, SYTOX® Green and Propidium iodide where tested against GelGreen™ (the reference method). In this example, the latter conditions outlined in example 6 and which were found to result in a good correlation between IBC/ml and CFU/ml, were used as the "reference method", namely i) using a staining composition comprising the same dilution of GelGreen™ (from Biotium) as described in Example 1 in a Tris-saline solution (200 mM Trizma® base, 150 mM NaCl, pH 10.6) and 0.12 KNPU/ml Savinase® 16L protease (from Novozymes), ii) using an incubation temperature of approximately 68° C. for 1 min., and iii) performing sonication for 5 seconds at 40 kHz both before and after the incubation. Nucleic acid dyes Evagreen®, SYTOX® Green and propidium iodide were tested using the same staining and incubation conditions as for the reference method only differing in the type of dye comprised in the staining composition. Evagreen® was used at a concentration of 1.25 µM in the staining composition. SYTOX® Green and Propidium iodide were used at a concentration of 5 µM in the staining composition. Three different types of milk were used: Locally obtained raw bulk tank milk from a farm and dairy plant where collected at a local farmer. This milk is referred to as fresh raw milk and is not older than 24 hours. 24 hour and 48 hour old milk were obtained from a dairy plant. Since fresh raw milk does not have a high bacterial count, it was spiked with live or dead E. coli cells, respectively. For this purpose E. coli was grown overnight (approx. 15 h) in TSB at 32° C. The dead bacterial where obtained by heating the grown E. coli at 110° C. for 10 minutes. An amount of 200 µl of E. coli (living or dead/damaged) is added to 45 ml fresh raw bulk milk. Both living and dead are from the same culture tube and exactly the same amount is put in the 45 ml Fresh raw milk. All the milk samples are kept at 4° C. until analyzed. The method of staining (and counting) bacteria in milk samples was performed as follows: 200 µl of unheated milk is diluted with 1800 µl staining composition and incubated at approximately 68° C. for 1 minute; the sample is sonicated for 5 seconds at 40 kHz both before and after the incubation. Finally, the samples were analyzed on the flow cytometer and the fluorescent signals from the bacteria were detected and a count per unit volume was determined. Purified water is used as negative controls (here referred to as blanc samples).

As can be seen in FIG. 13, for blanc samples, fresh bulk tank milk samples and 24 h old bulk tank milk samples EvaGreen® shows a good match with the standard reference method using GelGreen™ (see FIG. 13). For 48 h old bulk tank milk, milk spiked with E. coli and for milk spiked with E. coli and cooked for 10 minutes, EvaGreen® shows an IBC a little below the standard reference method using GelGreen™. However, these results are still good enough to be used for the purpose of quantifying IBC in bulk tank milk since the accuracy specifications for high (>1 million per ml) IBC numbers are lower than for low IBC numbers. Also, since the EvaGreen® results are lower at high IBC numbers compared to the standard reference method, these results can easily be compensated by a mathematical correction function. So, from these experimental results it can be concluded that EvaGreen® is a good cell impermeable alternative dye for GelGreen™.

SYTOX® Green shows (significant) higher IBC numbers compared to the standard GelGreen™ based reference method for fresh milk, 24 h old milk, 48 h old milk and spiked & cooked milk. For spiked milk however, the IBC is significant lower compared to the standard GelGreen™ based reference method. This proves that Sytox green does not stain bacteria (Sytox based spiked milk count is too low compared to GelGreen reference method) and that the background noise using Sytox Green is too high (too high count for the un-spiked samples). This conclusion is supported by the raw (dotplot) data from these experiments which is not shown here. Therefore it can be concluded that Sytox green does not work and therefore cannot be used as an alternative for Gelgreen.

Propidium iodide clearly does not work under the tested conditions. Almost no IBC counts are seen for the milk samples except for bulk tank milk spiked with E. coli and cooked for 10 minutes. This is in agreement with the specifications of propidium iodide since this dye only penetrates cell membranes of dead cells. Most likely, the cell membranes of the bacteria in the other milk samples are not damaged enough for Propidium iodide to pass through.

Example 8

Exploring Different Buffers

To investigate the usefulness of staining compositions with pH of approximately 10.6 but comprising other buffers or solutions than the Tris-saline solution used in examples 5-9, Tris buffer without NaCl (=Tris solution), CAPS buffer and Sodium bicarbonate buffer where tested against the "reference buffer", Tris-saline buffer (200 mM Trizma® base, 150 mM NaCl, pH 10.6). Apart from the buffer/solution, the staining composition and staining method used, was the same as in Example 7. For the comparison, different staining compositions were prepared replacing the 200 mM Trizma® base, 150 mM NaCl with either 200 mM Trizma® base and no NaCl, 100 mM CAPS titrated with NaOH to pH 10.6 (approximately 100 mM NaOH) or 200 mM Sodium bicarbonate titrated with NaOH to pH 10.6 (approximately 100 mM NaOH). Locally obtained raw bulk tank milk from a dairy plant and farmer where collected. 200 µL of unheated raw milk is diluted with 1800 µL staining composition and incubated at approximately 68° C. for 1 minute; the sample is sonicated for 5 seconds both before and after the incubation. Finally, the samples were analyzed on the flow cytometer and the fluorescent signals from the bacteria were detected and a count per unit volume was determined. Purified water is used as negative controls (here referred to as blanc samples).

Figure 14:
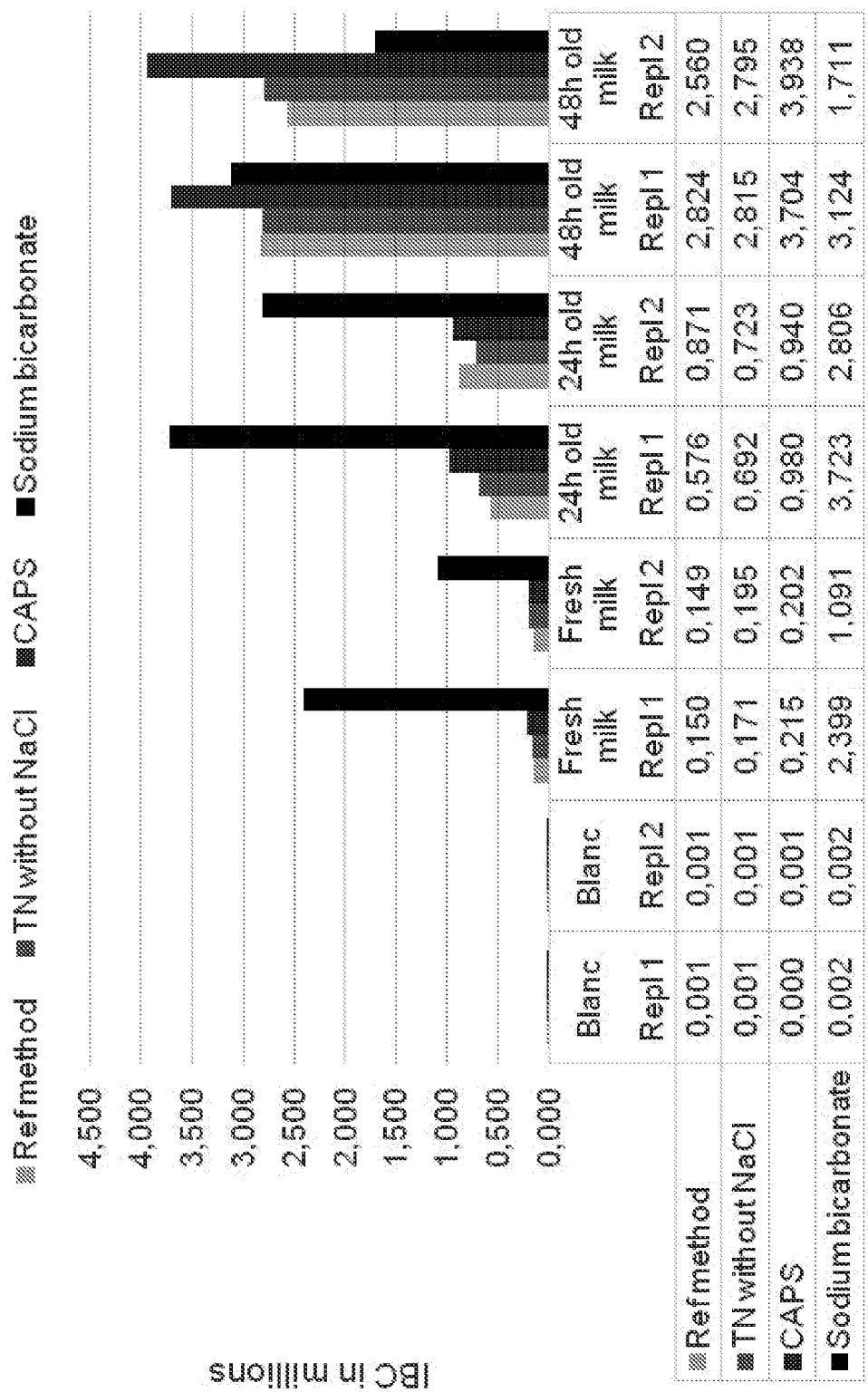
FIG. 14 shows a bar diagram of the four tested buffer agents for each of the tested samples. For each sample the bars from left to right are 1) the reference method (Tris-buffered saline), 2) Tris solution without NaCl (here referred to as "TN without NaCl", 3) CAPS and 4) Sodium bicarbonate. "Blanc" is purified water, "Fresh milk" is less than 24 hour old raw fresh milk obtained from local farmer, "24 h old milk" is 24 hour old milk obtained from milk factory and "48 h old milk" is 48 hour old milk obtained from milk factory. IBC numbers are given in million counts per ml.

From FIG. 14 it is clear that a Tris solution without NaCl is a good alternative for the Tris-saline solution. The IBC results are not statistical significant different from the standard Tris-saline solution used in the reference method. CAPS (CAPS=N-cyclohexyl-3-aminopropanesulfonic acid) buffer shows higher IBC numbers at high IBC samples. Since the accuracy at high IBC samples is less important compared to low IBC samples and the fact that this difference at high IBC numbers can easily be corrected by a mathematical correction function, it can be concluded that CAPS buffer is a good alternative for the standard Tris-saline saline as well.

Sodium bicarbonate buffer clearly does not work under the tested conditions. The IBC numbers on low IBC samples are much too high. Also, the variation between the 2 replicates for sodium bicarbonate is much too high resulting I a poor reproducibility and therefore inaccurate results. This is probably caused by high noise signals using this sodium bicarbonate buffer.

Example 9

Exploring Different Temperature Settings with Raw Milk Samples

In example 5 experimental results of the inventive method by using different temperature settings and saline liquid spiked with E. coli was discussed. After building a first serious prototype the final settings have been slightly adjusted to temperature preferably 68° C.

From example 5 it is already clear that temperatures lower than the optimal settings result in decreased DNA staining and so bacteria counting performance. Since these experiments were conducted with saline liquid and not with milk, additional experiments with raw milk samples have been conducted. Raw fresh milk and 24 hour old milk were obtained as described in example 7 and the raw fresh milk was spiked with live E. coli also as described in example 7. Milk samples were kept at 4° C. until analyzed. The method of staining (and counting) bacteria in raw milk was performed by the reference method as described in example 7.

Figure 15:
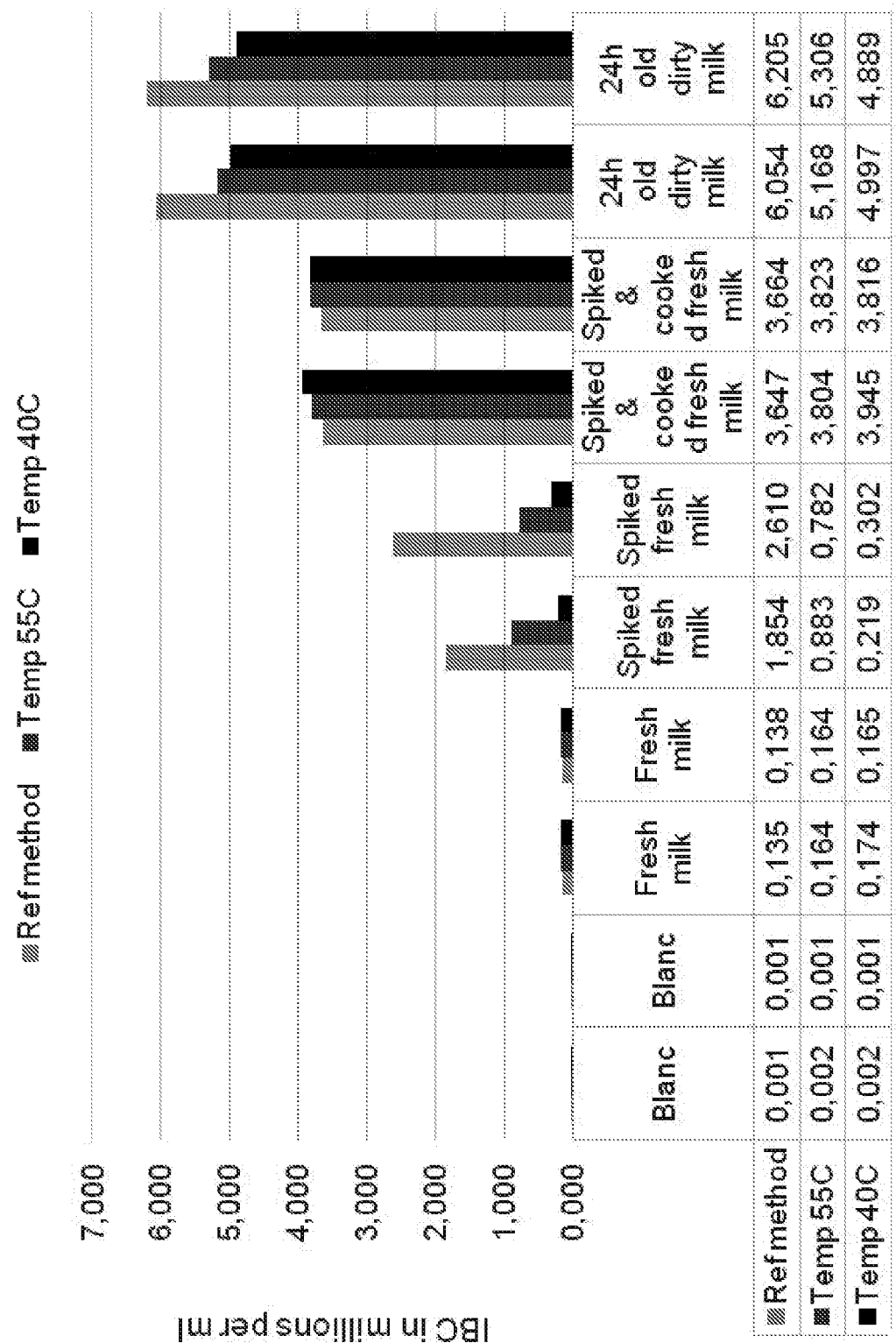
FIG. 15 shows a bar diagram of three tested temperatures for each of the tested samples. For each sample the bars from left to right are 1) the reference method (68° C.), 2) 55° C. and 3) 40° C. "Blanc" is purified water, "Fresh milk" is less than 24 hour old raw fresh milk obtained from local farmer, "spiked fresh milk" is raw fresh milk spiked with live *E. coli*, "spiked and cooked fresh milk" is raw fresh milk spiked with cooked (dead) *E. coli* and "24 h old dirty milk" is 24 hour old milk obtained from milk factory with a higher bacterial count than normal. IBC numbers are given in million counts per ml.

From the results shown in FIG. 15 more or less the same conclusions as from example 5 can be made. Lowering temperature settings decreases the bacteria counting performance. For 40° C. temperature settings for example, it can be seen that the IBC numbers for fresh spiked milk are way too low compared to the standard 68° C. based reference method.

Figure 16:
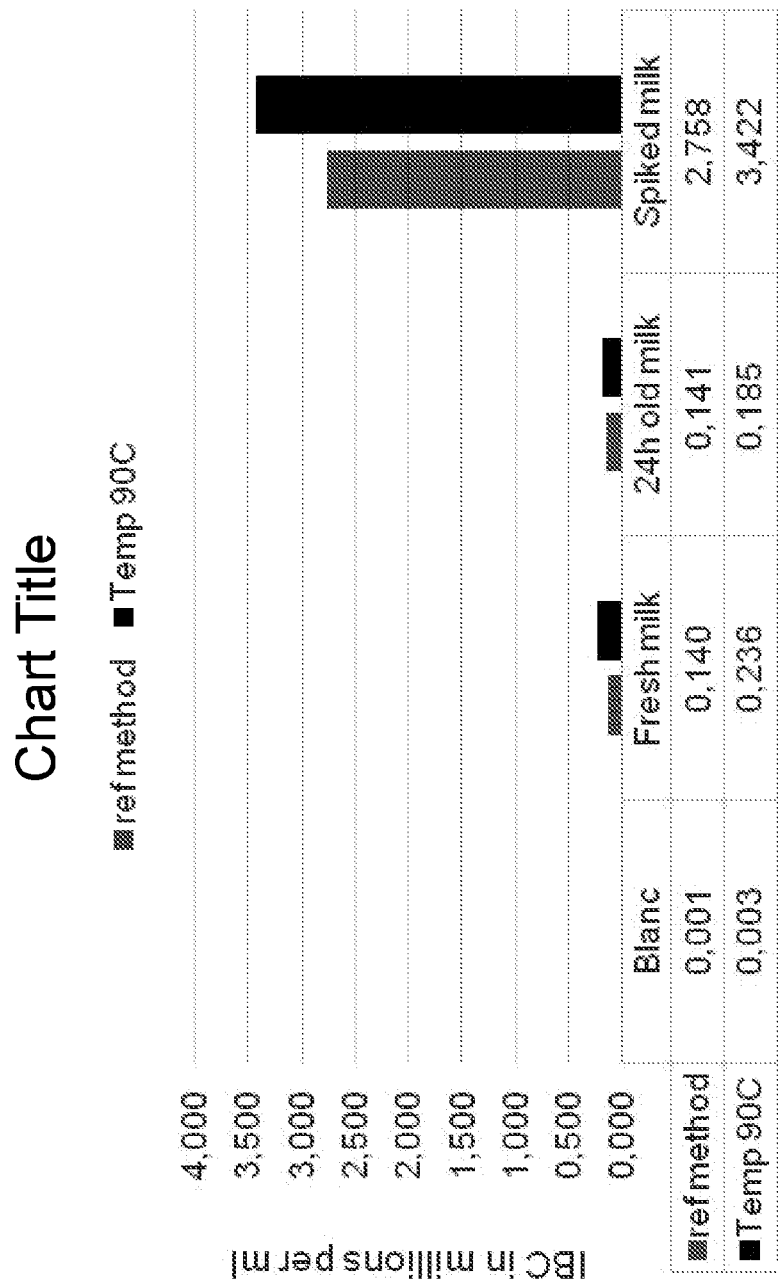
FIG. 16 shows a bar diagram of two tested temperatures for each of the tested samples. For each sample the bars from left to right are 1) the reference method (68° C.) and 2) 90° C. "Blanc" is purified water, "Fresh milk" is less than 24 hour old raw fresh milk obtained from local farmer, "24 h old milk" is 24 hour old milk obtained from milk factory and "spiked milk" is raw fresh milk spiked with live *E. coli*. IBC numbers are given in million counts per ml.

In FIG. 16 the results from raw milk experiments at a temperature of 90° C. are shown. The IBC results for all the samples are slightly higher compared to the 68° C. based reference method. Since the IBC results for the blanc samples are also (significant) higher, the cause of these higher IBC numbers is probably due to higher noise signal levels at 90° C. However, the results are in such a good agreement that it can be concluded that a temperature of 90° C. still works fine. Most likely, a temperature up to 100° C. will work fine as well although at these high temperatures some practical limitations might arise.

Example 10

Exploring Different pH Settings with Raw Milk Samples

Fresh raw milk and 24 hour old milk were obtained as described in example 7 and the raw fresh milk was spiked with live and dead *E. coli*, respectively, also as described in example 7. Milk samples were kept at 4° C. until analyzed. The reference method of staining, incubation and counting of bacteria in raw milk using a staining composition comprising a Tris-saline solution at pH=10.6 was performed as described in example 7. For the other pH values tested the staining compositions differed from the staining composition of the reference method by that the Tris-saline solution of pH=10.6 was titrated to pH=8.7 and 7.0, respectively.

Figure 17:
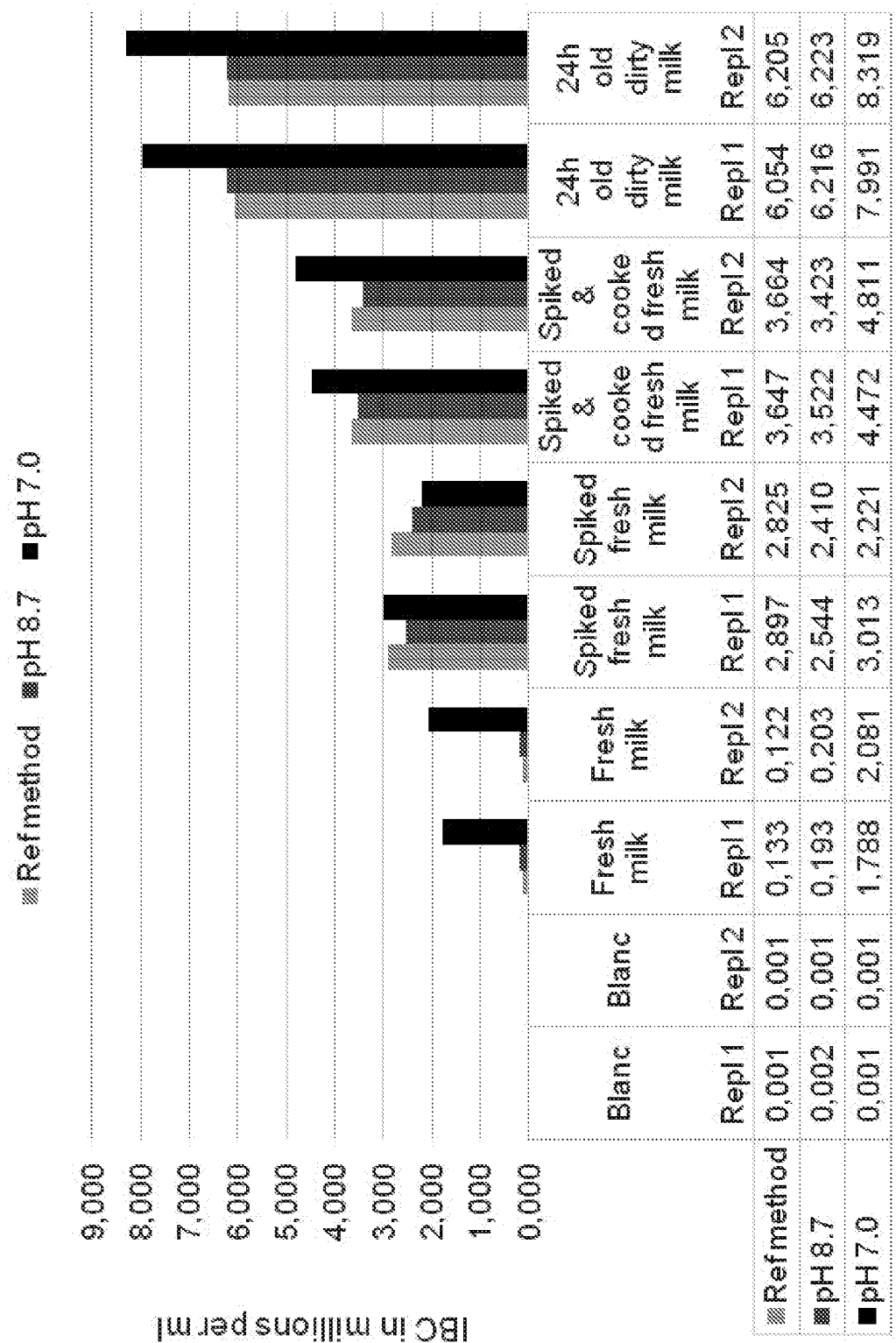
FIG. 17 shows a bar diagram of the three tested dyes for each of the tested samples. For each sample the bars from left to right are 1) the reference method (pH=10.6), 2) pH=8.7 and 3) pH=7.0. "Blanc" is purified water, "Fresh milk" is less than 24 hour old raw fresh milk obtained from local farmer, "spiked fresh milk" is raw fresh milk spiked with live *E. coli*, "spiked and cooked milk" is raw fresh milk spiked with cooked (dead) *E. coli* and "24 h old dirty milk" is 24 hour old milk obtained from milk factory with a higher bacterial count than normal. IBC numbers are given in million counts per ml.

From the results shown in FIG. 17 it can be seen that using a pH of 8.7 instead of a pH of the standard setting of 10.6 also gives good results. The IBC numbers are comparable with the reference method. A pH of 7.0 however clearly does not work anymore. The IBC numbers at low IBC milk samples are way too high (more than 1.5 million counts per ml higher compared to the reference method for fresh milk for example). Therefore the pH range of the claims is defined between a pH from about 8 to about 11.5, from about 8 to about 8, from about 8 to about 10.6 or from about 8.5 to about 10.6.

Advantageous Embodiments are Set Out in the Following Clauses

1. A method of counting cells in a liquid sample, said method comprising the steps of:
   a) mixing a protease with a nucleic acid dye that is cell-impermeant at room temperature and neutral pH, to form a staining composition;
   b) mixing said staining composition with said sample;
   c) optionally sonicating the mixture of step b);
   d) incubating the mixture at 40 to 70° C., preferably at 60 to 68° C., more preferably at 62° C.;
   e) optionally sonicating the incubated mixture of step d); and
   f) counting the cells that are stained with said dye within said mixture, or a part thereof.
2. A method according to clause 1, wherein said cells are somatic and/or bacterial cells.
3. A method according to clause 1 or 2, wherein said liquid sample is a biological sample selected from the group consisting of milk, blood, urine, saliva, feces and spinal fluid.
4. A method according to clause 1 or 2, wherein said liquid sample is an environmental sample, such as waste water.
5. A method according to any one of clauses 1 to 4, wherein said staining composition has a pH that makes said nucleic acid dye cell-permeable.
6. A method according to clause 5, wherein said staining composition has a pH of 8 to 10.6, and wherein said incubation takes place at a pH in the range of 8 to 10.6.
7. A method according to any one of clauses 1 to 6, wherein said protease and said nucleic acid dye are mixed in a Tris-NaCl buffer to form said staining composition.
8. A method according to any one of clauses 1 to 7, wherein said staining composition is heated to 40 to 70° C., preferably to 60 to 68° C., more preferably to 62° C., before it is mixed with said sample.
9. A method according to any one of clauses 1 to 8, wherein said sample is heated to 40 to 70° C., preferably to 60 to 68° C., more preferably to 62° C., before or when it is mixed with said staining composition.
10. A method according to any one of clauses 1 to 9, wherein said nucleic acid dye is a dye from the GelGreen™ or GelRed™ family of dyes, preferably 10, 10'-(6, 22-dioxo-11, 14, 17-trioxa-7, 21-diazaheptacosane-1, 27-diyl) bis (3, 6-bis (dimethylamino) acridin-10-ium) iodide).
11. A method according to any one of clauses 1 to 10, wherein said protease is a protease type subtilisin.
12. A method according to any one of clauses 1 to 11, wherein the stained cells are counted by using a fluorescence detecting instrument, such as a flow cytometer, a fluorescence microscope or fluorescent imaging system, a fluorometer or a fluorescence plate reader.
13. A method of making a nucleic acid dye from the GelGreen™ or GelRed™ family of dyes cell-permeant, said method comprising the steps of maintaining said dye at a pH of 8 to 10.6 in a suitable buffer and heating said dye in said buffer to a temperature of 40 to 70° C., preferably to a temperature of 60 to 68° C., more preferably to a temperature of 62° C.
14. An apparatus for counting somatic and/or bacterial cells in a liquid sample, the apparatus comprising:
   a mixing cup for combining the liquid sample with a staining composition to obtain a mixture;
   a sample inlet for providing the liquid sample to the mixing cup;
   a staining composition inlet for providing the staining composition to the mixing cup;
   a heating element for heating the mixing cup and the mixture to an appropriate temperature of 40 to 70° C., preferably to a temperature of 60 to 68° C., more preferably to a temperature of 62° C.;
   optionally a sonicator for providing energy in the form of ultrasound to the mixture, wherein the tip of the sonicator is arranged in the mixture or placed against the mixing cup;
   an outlet for obtaining the mixture or a part thereof, and providing said mixture or said part thereof to a measurement module; and
   the measurement module for counting stained cells in said mixture, or in said part thereof.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of counting cells in a liquid sample, said method comprising the steps of:
   a) mixing a staining composition comprising a dimeric nucleic acid dye and a buffering agent with said sample;
   b) optionally sonicating the mixture of step a);
   c) incubating the mixture at a temperature from about 50° C. to about 95° C. for less than 10 minutes, wherein the mixture is incubated without an ion-chelating agent or detergent;
   d) optionally sonicating the incubated mixture of step c); and
   e) counting the cells that are stained with said dye within said mixture, or a part thereof, wherein
   the dimeric nucleic acid dye is cell-impermeant to HeLa cells after 30 minutes of incubation at 37° C. and neutral pH and has the formula Q1-BRIDGE-Q2, wherein Q1 and Q2 are nucleic acid dye moieties and BRIDGE is connecting Q1 and Q2 and has the formula:

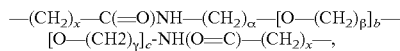

wherein:
   each x, independently, is an integer selected from 1 to 11,
   α may be an integer selected from 2 to about 20,
   β and γ, are independently zero, 2 or 3,
   b is zero or an integer selected from 1 to about 20, and
   c is zero, 1 or 2, and wherein
   the buffering agent is an organic buffering agent comprising an amine which is effective in rendering the dimeric nucleic acid dye cell-permeant under the incubating conditions of step c) to achieve a reliable counting of the cells.

2. The method according to claim 1, wherein the dimeric nucleic acid dye is capable of binding to DNA via a release-on-demand mechanism.

3. The method according to claim 2, wherein the BRIDGE is a substantially aliphatic, substantially neutral linker comprising from about 8 to about 150 non-hydrogen atoms.

4. A method according to claim 1, wherein
   each x is 5,
   α is 2 or 3,
   β is 2,
   b is 1 or 2
   c is zero, 1 or 2, and
   γ is 3, when c is 1 or 2.

5. The method according to claim 4, wherein BRIDGE has a formula selected from the group consisting of:

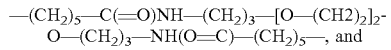   a)

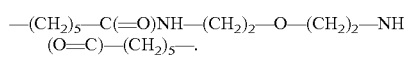   b)

6. The method according to claim 1, wherein Q1 and/or Q2 is a fluorescent nucleic acid dye moiety.

7. The method according to claim 6, wherein the fluorescent nucleic acid dye moiety is derived from a nucleic acid dye selected from the group consisting of an acridine-based nucleic acid dye, an asymmetric cyanine-based nucleic acid dye, a phenanthridinium-based nucleic acid dye, a symmetric cyanine-based nucleic acid dye, a pyronin nucleic acid dye, a styryl nucleic acid dye, a derivative of DAPI, and a derivative of a Hoechst dye.

8. The method according to claim 7, wherein the fluorescent nucleic acid dye moiety is derived from a nucleic acid dye selected from the group consisting of an acridine-based nucleic acid dye and a phenanthridinium-based nucleic acid dye.

9. The method according to claim 1, wherein Q1 and Q2 are the same.

10. The method according to claim 1, wherein the staining composition further comprises a protease.

11. The method according to claim 1, wherein said cells are somatic and/or bacterial cells.

12. The method according to claim 1, wherein the liquid sample is milk, said method comprising the steps of:
   a) mixing a staining composition comprising a dimeric nucleic acid dye, a protease and a buffering agent with said milk;
   b) optionally sonicating the mixture of step a) for about 1 to about 10 seconds at from about 15 to about 50 kHz;
   c) incubating the mixture at a temperature from about 62° C. to about 68° C. for about 1 minute to about 5 minutes;
   d) optionally sonicating the incubated mixture of step c) for about 1 to about 10 seconds at from about 15 to about 50 kHz, and
   e) counting the cells that are stained with said dye within said mixture, or a part thereof, using a flow cytometer;
wherein,
   the dimeric nucleic acid dye has the formula Q1-BRIDGE-Q2, wherein Q1 and Q2 are nucleic acid dye moieties connected by BRIDGE, and
   Q1 and Q2 are the same and are selected from the group consisting of nucleic acid dye moieties having structure I and structure III,

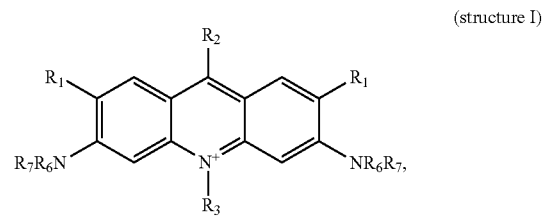

wherein:
   each R1 is independently selected from the group consisting of H, a C1-C2 group, and an alkyl,
   BRIDGE is attached to R2 or R3,
   when BRIDGE is attached to R2, R3 is selected from the group consisting of H or —CH3,
   when BRIDGE is attached to R3, R2 is selected from the group consisting of H, —CH3, —NH2, —NHCH3, —CN, and —C(=O)NH2,
   each of R6 and R7 is independently selected from the group consisting of H, a C1-C2 group and an alkyl, and
   ψ is an anion that balances positive charge(s) associated with the dye

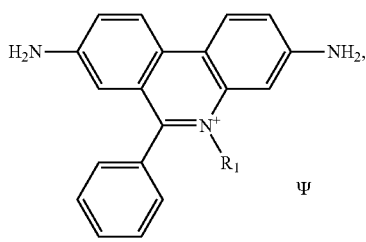 (structure III)

wherein,
BRIDGE is attached to R1, and
ψ is an anion that balances positive charge(s) associated with the dye;
wherein
BRIDGE has a formula selected from the group consisting of

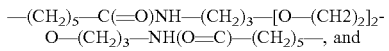

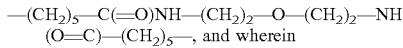

the buffering agent is Tris.

13. The method according to claim 12, wherein the milk is cow milk.

14. The method according to claim 10, wherein the protease is a serine endopeptidase.

15. The method according to claim 1, wherein said staining composition has a pH from about 8 to about 11.5.

16. The method according to claim 1, wherein step c) is performed at a temperature from about 60 to about 70° C.

17. The method according to claim 1, further comprising preheating the staining composition to a temperature of from about 45 to about 95° C., prior to mixing with the sample.

18. The method according to claim 1, wherein the dimeric nucleic acid dye is 10, 10'-(6, 22-dioxo-11, 14, 17-trioxa-7, 21-diazaheptacosane-1, 27-diyl) bis (3, 6-bis (dimethylamino) acridin-10-ium) iodide) and the buffering agent is Tris.

19. A method of counting cells in a liquid sample, said method comprising the steps of:
   a) mixing a staining composition comprising a dimeric nucleic acid dye and an amine buffering agent with said sample;
   b) optionally sonicating the mixture of step a);
   c) incubating the mixture at a temperature from about 50° C. to about 95° C. for less than 10 minutes, wherein the mixture is incubated without an ion-chelating agent or detergent;
   d) optionally sonicating the incubated mixture of step c); and
   e) counting the cells that are stained with said dye within said mixture, or a part thereof, wherein
   the dimeric nucleic acid dye is cell-impermeant to HeLa cells after 30 minutes of incubation at 37° C. and neutral pH and has the formula Q1-BRIDGE-Q2, wherein Q1 and Q2 are nucleic acid dye moieties and BRIDGE is connecting Q1 and Q2 and has the formula:

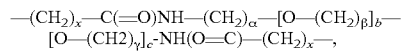

wherein:
each x, independently, is an integer selected from 1 to 11,
α may be an integer selected from 2 to about 20,
β and γ, are independently zero, 2 or 3,
b is zero or an integer selected from 1 to about 20, and
c is zero, 1 or 2.

20. The method of claim 1, wherein step c) is performed at a temperature from about 62° C. to about 68° C.

* * * * *